US009074220B2

(12) United States Patent
Mauro et al.

(10) Patent No.: US 9,074,220 B2
(45) Date of Patent: *Jul. 7, 2015

(54) TRANSLATION ENHANCER-ELEMENT DEPENDENT VECTOR SYSTEMS

(75) Inventors: Vincent P. Mauro, San Diego, CA (US); Gerald M. Edelman, La Jolla, CA (US); Wei Zhou, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/857,286

(22) Filed: Aug. 16, 2010

(65) Prior Publication Data

US 2011/0124100 A1    May 26, 2011

Related U.S. Application Data

(63) Continuation of application No. 11/509,293, filed on Aug. 23, 2006.

(60) Provisional application No. 60/711,149, filed on Aug. 24, 2005.

(51) Int. Cl.
| | |
|---|---|
| C12N 15/00 | (2006.01) |
| C07H 21/02 | (2006.01) |
| C07H 21/04 | (2006.01) |
| C12N 15/85 | (2006.01) |
| C12N 15/10 | (2006.01) |
| C12N 15/67 | (2006.01) |

(52) U.S. Cl.
CPC ............ *C12N 15/85* (2013.01); *C12N 15/1051* (2013.01); *C12N 15/1086* (2013.01); *C12N 15/67* (2013.01); *C12N 2800/107* (2013.01); *C12N 2830/002* (2013.01); *C12N 2840/105* (2013.01); *C12N 2840/20* (2013.01); *C12N 2840/203* (2013.01)

(58) Field of Classification Search
CPC ........... C12N 15/1051; C12N 15/1086; C12N 15/67; C12N 15/85; C12N 2800/107
USPC .............................. 435/320.1; 536/23.1, 24.1
See application file for complete search history.

(56) References Cited

U.S. PATENT DOCUMENTS

| 6,524,792 B1 | 2/2003 | Renner et al. | |
|---|---|---|---|
| 7,262,051 B2 * | 8/2007 | Wu et al. .................... | 435/320.1 |

FOREIGN PATENT DOCUMENTS

| WO | WO 99/25876 A1 | 5/1999 |
|---|---|---|
| WO | WO 99/25896 A1 | 5/1999 |
| WO | WO 01/55369 A1 | 8/2001 |

OTHER PUBLICATIONS

Li et al Stable expression of three genes from a tricistronic retroviral vector containing a picornavirus and 9-nt cellular internal ribosome entry site elements Journal of Virological Methods 115 (2004) 137-144.*
Watson et al., 2007 by W. H. Freeman and Company Recombinant DNA, Third Edition, pp. 121-122.*
Chapell et al., Ribosomal tethering and clustering as mechanisms for translation initiation PNAS Nov. 28, 2006 vol. 103 No. 48 18077-18082.*
Sadowski et al., GAL4-VP16 is an unusually potent transcriptional activator Nature. Oct. 6, 1988;335(6190):563-4.*
Zhou et al. "A Positive Feedback Vector for Identification of Nucleotide Sequences that Enhance Translation", *Proceeding of the National Academy of Sciences*, 102(18):6273-6278 (2005).
Fussenegger et al., "Regulated multicistronic expression technology for mammalian metabolic engineering", *Cytotechnology*, 28(1-3):111-125 (1998).
Owens et al., "Identification of two short internal ribosome entry sites selected from libraries of random oligonucleotides", *Proc. Natl. Acad. Sci. USA.*, 98(4):1471-1476 (2001).
Zhou et al., "Isolation and identification of short nucleotide sequences that affect translation initiation in *Saccharomyces cerevisiae*", *Proc. Natl. Acad. Sci. USA.*, 100(8):4457-4462 (2003).
Vende et al., "Efficient translation of rotavirus mRNA requires simultaneous interaction of NSP3 with the eukaryotic translation initiation factor eIF4G and the mRNA 3' end", *J. Virol.*, 74(15):7064-7071 (2000).
Communication from European Patent Office from application No. EP 06 802 211.0.
Communication from European Patent Office from application No. EP 11 181 999.1.
Communication pursuant to Article 94(3) EPC dated Aug. 1, 2014 for corresponding European Patent Application No. 11181999.1 (7 pgs.).
Canadian Office Action dated Jun. 5, 2014 for corresponding Canadian Patent Application No. 2,620,420 (3 pgs.).
Fussenegger, M. et al., "Autoregulated Multicistronic Expression Vectors Provide One-Step Cloning of Regulated Product Gene Expression in Mammalian Cells", Biotechnology Progress, vol. 13, No. 6, 1997, pp. 733-740.
Padilla-Noriega, L. et al., "Rotavirus Protein NSP3 Shuts Off Host Cell Protein Synthesis", Virology, vol. 298, No. 1, 2002, pp. 1-7.
Communication pursuant to Article 94(3) EPC, dated Aug. 1, 2014, for EP Application No. 06802211.0.

* cited by examiner

*Primary Examiner* — Maria Leavitt
(74) *Attorney, Agent, or Firm* — Cooley LLP; Ivor R. Elrifi; Christina K. Stock

(57) ABSTRACT

A translation enhancer-driven positive feedback vector system is disclosed which is designed to facilitate identification of a Translational Enhancer Element (TEE) and to provide a means for overexpression of gene products. The system exploits both transcriptional and translational approaches to control the expression levels of genes and/or gene products. Methods are also disclosed for screening libraries of random nucleotide sequences to identify translational elements and for overproduction of proteins, which have uses in both research and industrial environments.

4 Claims, 12 Drawing Sheets

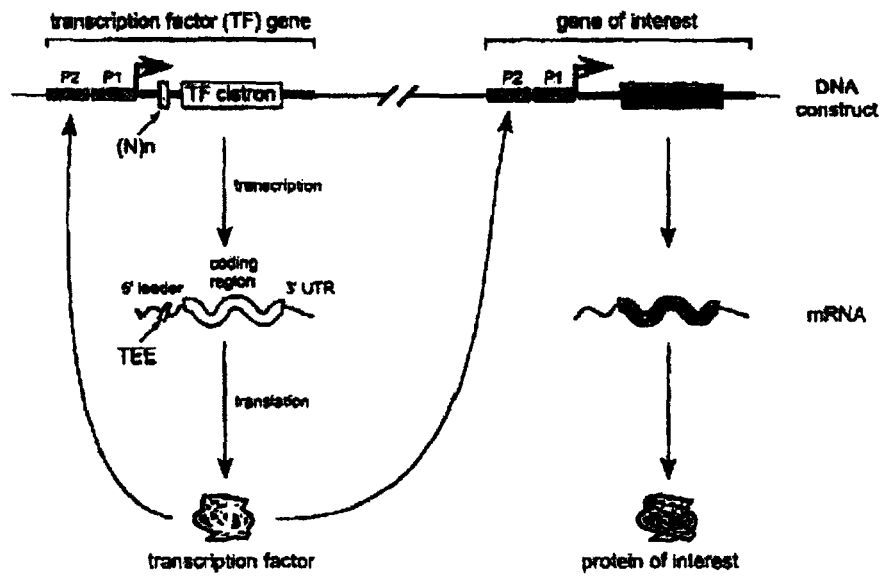

Promoter elements:
- P1: - minimal promoter (TATA)
  - regulatable promoter
- P2: - upstream activating sequence (UAS; one to multiple copies)
  - T7 promoter
  - other transcription elements Transcription factor genes:
- GAL4, GAL4/VP16
- T7 RNA polymerase
- other transcription factors Genes of Interest:
- fluorescent protein genes (e.g. enhanced green fluorescent protein; EGFP)
- luciferase genes (*Renilla* or *Photinus*)
- therapeutic protein (e.g. monoclonal antibodies)

Figure 1

Sequences and one cut enzymes: pUAS-GV16-UAS-EGFP

```
        KpnI
Acc65I   |
     | (ASP718)                                         UAS
     GGTACCGAGCTCAAGCTTCGGAGTACTGTCCTCCGAGCGGAGTACTGTCCTCCGAGCGGA
  1  ---------+---------+---------+---------+---------+---------+  60
     CCATGGCTCGAGTTCGAAGCCTCATGACAGGAGGCTCGCCTCATGACAGGAGGCTCGCCT

BstBI(CSP45I)
                                    |
     GTACTGTCCTCCGAGCGGAGTACTGTCCTCCGTTCGAAAGCGGACCCCTGGCAGGAGGAA
  61 ---------+---------+---------+---------+---------+---------+ 120
     CATGACAGGAGGCTCGCCTCATGACAGGAGGCAAGCTTTCGCCTGGGGACCGTCCTCCTT

GGTCAGCAGAGCTGCTGATAAGAGCCGTATAAAGAGGGTTCCGCTCGCAAAGATCTATGG
 121 ---------+---------+---------+---------+---------+---------+ 180
     CCAGTCGTCTCGACGACTATTCTCGGCATATTTCTCCCAAGGCGAGCGTTTCTAGATACC
        EcoRI                     BamHI
          |                         |
     CATGAATTCNNNNNNNNNNNNNNNNNNNNNNGGATCCATGGTGAAGCTGTCTTCTATCGAACAA
 181 ---------+---------+---------+---------+---------+---------+ 240
     GTACTTAAGNNNNNNNNNNNNNNNNNNNNNNCCTAGGTACCACTTCGACAGAAGATAGCTT GTT
                                        M  V  K  L  S  S  I  E  Q  -
           GAL4R1
     GCATGCGATATTTGCCGACTTAAAAAGCTCAAGTGCTCCAAAGAAAAACCGAAGTGCGCC
 241 ---------+---------+---------+---------+---------+---------+ 300
     CGTACGCTATAAACGGCTGAATTTTTCGAGTTCACGAGGTTTCTTTTTGGCTTCACGCGG
      A  C  D  I  C  R  L  K  K  L  K  C  S  K  E  K  P  K  C  A   -
           GAL4R2                                          GAL4R3
     AAGTGTCTGAAGAACAACTGGGAGTGTCGCTACTCTCCCAAAACCAAAAGGTCTCCGCTG
 301 ---------+---------+---------+---------+---------+---------+ 360
     TTCACAGACTTCTTGTTGACCCTCACAGCGATGAGAGGGTTTTGGTTTTCCAGAGGCGAC
      K  C  L  K  N  N  W  E  C  R  Y  S  P  K  T  K  R  S  P  L   -
                                                  GAL4R4
     ACTAGGGCACATCTGACAGAAGTGGAATCAAGGCTAGAAAGACTGGAACAGCTATTTCTA
 361 ---------+---------+---------+---------+---------+---------+ 420
     TGATCCCGTGTAGACTGTCTTCACCTTAGTTCCGATCTTTCTGACCTTGTCGATAAAGAT
      T  R  A  H  L  T  E  V  E  S  R  L  E  R  L  E  Q  L  F  L   -
           XhoI
             |
     CTGATTTTTCCTCGAGAAGACCTTGACATGATTTTGAAAATGGATTCTTTACAGGATATA
 421 ---------+---------+---------+---------+---------+---------+ 480
     GACTAAAAAGGAGCTCTTCTGGAACTGTACTAAAACTTTTACCTAAGAAATGTCCTATAT
      L  I  F  P  R  E  D  L  D  M  I  L  K  M  D  S  L  Q  D  I   -

AAAGCATTGTTAACAGGATTATTTGTACAAGATAATGTGAATAAAGATGCCGTCACAGAT
 481 ---------+---------+---------+---------+---------+---------+ 540
     TTTCGTAACAATTGTCCTAATAAACATGTTCTATTACACTTATTTCTACGGCAGTGTCTA
      K  A  L  L  T  G  L  F  V  Q  D  N  V  N  K  D  A  V  T  D   -

AGATTGGCTTCAGTGGAGACTGATATGCCTCTAACATTGAGACAGCATAGAATAAGTGCG
 541 ---------+---------+---------+---------+---------+---------+ 600
     TCTAACCGAAGTCACCTCTGACTATACGGAGATTGTAACTCTGTCGTATCTTATTCACGC
      R  L  A  S  V  E  T  D  M  P  L  T  L  R  Q  H  R  I  S  A   -
```

Figure 4

```
            ACATCATCATCGGAAGAGAGTAGTAACAAAGGTCAAAGACAGTTGACTGTATCGATTAAA
  601     ---------+---------+---------+---------+---------+---------+  660
            TGTAGTAGTAGCCTTCTCTCATCATTGTTTCCAGTTTCTGTCAACTGACATAGCTAATTT
             T  S  S  S  E  E  S  S  N  K  G  Q  R  Q  L  T  V  S  I  K   -
            GTCGCCCCCCCGACCGATGTCAGCCTGGGGGACGAGCTCCACTTAGACGGCGAGGACGTG
  661     ---------+---------+---------+---------+---------+---------+  720
            CAGCGGGGGGGCTGGCTACAGTCGGACCCCCTGCTCGAGGTGAATCTGCCGCTCCTGCAC
             V  A  P  P  T  D  V  S  L  G  D  E  L  H  L  D  G  E  D  V   -

GCGATGGCGCATGCCGACGCGCTAGACGATTTCGATCTGGACATGTTGGGGGACGGGGAT
  721     ---------+---------+---------+---------+---------+---------+  780
            CGCTACCGCGTACGGCTGCGCGATCTGCTAAAGCTAGACCTGTACAACCCCCTGCCCCTA
             A  M  A  H  A  D  A  L  D  D  F  D  L  D  M  L  G  D  G  D   -
                  SmaI
                  XmaI |
                   |  |
            TCCCCGGGGCCGGGATTTACCCCCCACGACTCCGCCCCCTACGGCGCTCTGGATATGGCC
  781     ---------+---------+---------+---------+---------+---------+  840
            AGGGGCCCCGGCCCTAAATGGGGGGTGCTGAGGCGGGGATGCCGCGAGACCTATACCGG
             S  P  G  P  G  F  T  P  H  D  S  A  P  Y  G  A  L  D  M  A   -
                                VP16-FOR
            GACTTCGAGTTTGAGCAGATGTTTACCGATGCCCTTGGAATTGACGAGTACGGTGGGTAA
  841     ---------+---------+---------+---------+---------+---------+  900
            CTGAAGCTCAAACTCGTCTACAAATGGCTACGGGAACCTTAACTGCTCATGCCACCCATT
             D  F  E  F  E  Q  M  F  T  D  A  L  G  I  D  E  Y  G  G  *   -
            SacII(KSP1)
                  |
            CCGCGGGCTAGAGTCGGGGCGGCCGGCCGCTTCGAGCAGACATGATAAGATACATTGATG
  901     ---------+---------+---------+---------+---------+---------+  960
            GGCGCCCGATCTCAGCCCCGCCGGCCGGCGAAGCTCGTCTGTACTATTCTATGTAACTAC

AGTTTGGACAAACCACAACTAGAATGCAGTGAAAAAAATGCTTTATTTGTGAAATTTGTG
  961     ---------+---------+---------+---------+---------+---------+ 1020
            TCAAACCTGTTTGGTGTTGATCTTACGTCACTTTTTTTACGAAATAAACACTTTAAACAC

ATGCTATTGCTTTATTTGTAACCATTATAAGCTGCAATAAACAAGTTAACAACAACAATT
 1021     ---------+---------+---------+---------+---------+---------+ 1080
            TACGATAACGAAATAAACATTGGTAATATTCGACGTTATTTGTTCAATTGTTGTTGTTAA

GCATTCATTTTATGTTTCAGGTTCAGGGGGAGGTGTGGGAGGTTTTTTAAAGCAAGTAAA
 1081     ---------+---------+---------+---------+---------+---------+ 1140
            CGTAAGTAAAATACAAAGTCCAAGTCCCCCTCCACACCCTCCAAAAAATTTCGTTCATTT

ACCTCTACAAATGTGGTAAAATCGATAAGGATCGATCCGTCGAGATCTGCGATCTAAGTA
 1141     ---------+---------+---------+---------+---------+---------+ 1200
            TGGAGATGTTTACACCATTTTAGCTATTCCTAGCTAGGCAGCTCTAGACGCTAGATTCAT
                  PstI
                    |                            UAS
            AGCTTGGCTGCAGGTCGACGGATCGGAGTACTGTCCTCCGAGCGGAGTACTGTCCTCCGA
 1201     ---------+---------+---------+---------+---------+---------+ 1260
            TCGAACCGACGTCCAGCTGCCTAGCCTCATGACAGGAGGCTCGCCTCATGACAGGAGGCT
                                UAS
            GCGGAGTACTGTCCTCCGAGCGGAGTACTGTCCTCCGAGCGGACCCCTGGCAGGAGGAAG
 1261     ---------+---------+---------+---------+---------+---------+ 1320
            CGCCTCATGACAGGAGGCTCGCCTCATGACAGGAGGCTCGCCTGGGGACCGTCCTCCTTC
```

Figure 4 (cont'd)

```
         GTCAGCAGAGCTGCTGATAAGAGCCGTATAAAGAGGGTTCCGCTCATGGCAAGGGGCAGT
1321   ---------+---------+---------+---------+---------+---------+ 1380
         CAGTCGTCTCGACGACTATTCTCGGCATATTTCTCCCAAGGCGAGTACCGTTCCCCGTCA

GGTCTCGGGATCTGAGCTTGGCATTCCGGTACTGTTGGTAAACCATGGTGAGCAAGGGCG
1381   ---------+---------+---------+---------+---------+---------+ 1440
         CCAGAGCCCTAGACTCGAACCGTAAGGCCATGACAACCATTTGGTACCACTCGTTCCCGC
                                                      M   V   S   K   G   E -

AGGAGCTGTTCACCGGGGTGGTGCCCATCCTGGTCGAGCTGGACGGCGACGTAAACGGCC
1441   ---------+---------+---------+---------+---------+---------+ 1500
         TCCTCGACAAGTGGCCCCACCACGGGTAGGACCAGCTCGACCTGCCGCTGCATTTGCCGG
           E   L   F   T   G   V   V   P   I   L   V   E   L   D   G   D   V   N   G   H -

ACAAGTTCAGCGTGTCCGGCGAGGGCGAGGGCGATGCCACCTACGGCAAGCTGACCCTGA
1501   ---------+---------+---------+---------+---------+---------+ 1560
         TGTTCAAGTCGCACAGGCCGCTCCCGCTCCCGCTACGGTGGATGCCGTTCGACTGGGACT
             K   F   S   V   S   G   E   G   E   G   D   A   T   Y   G   K   L   T   L   K -

AGTTCATCTGCACCACCGGCAAGCTGCCCGTGCCCTGGCCCACCCTCGTGACCACCCTGA
1561   ---------+---------+---------+---------+---------+---------+ 1620
         TCAAGTAGACGTGGTGGCCGTTCGACGGGCACGGGACCGGGTGGGAGCACTGGTGGGACT
             F   I   C   T   T   G   K   L   P   V   P   W   P   T   L   V   T   T   L   T -

CCTACGGCGTGCAGTGCTTCAGCCGCTACCCCGACCACATGAAGCAGCACGACTTCTTCA
1621   ---------+---------+---------+---------+---------+---------+ 1680
         GGATGCCGCACGTCACGAAGTCGGCGATGGGGCTGGTGTACTTCGTCGTGCTGAAGAAGT
             Y   G   V   Q   C   F   S   R   Y   P   D   H   M   K   Q   H   D   F   F   K -

AGTCCGCCATGCCCGAAGGCTACGTCCAGGAGCGCACCATCTTCTTCAAGGACGACGGCA
1681   ---------+---------+---------+---------+---------+---------+ 1740
         TCAGGCGGTACGGGCTTCCGATGCAGGTCCTCGCGTGGTAGAAGAAGTTCCTGCTGCCGT
             S   A   M   P   E   G   Y   V   Q   E   R   T   I   F   F   K   D   D   G   N -

ACTACAAGACCCGCGCCGAGGTGAAGTTCGAGGGCGACACCCTGGTGAACCGCATCGAGC
1741   ---------+---------+---------+---------+---------+---------+ 1800
         TGATGTTCTGGGCGCGGCTCCACTTCAAGCTCCCGCTGTGGGACCACTTGGCGTAGCTCG
             Y   K   T   R   A   E   V   K   F   E   G   D   T   L   V   N   R   I   E   L -

TGAAGGGCATCGACTTCAAGGAGGACGGCAACATCCTGGGGCACAAGCTGGAGTACAACT
1801   ---------+---------+---------+---------+---------+---------+ 1860
         ACTTCCCGTAGCTGAAGTTCCTCCTGCCGTTGTAGGACCCCGTGTTCGACCTCATGTTGA
             K   G   I   D   F   K   E   D   G   N   I   L   G   H   K   L   E   Y   N   Y -

ACAACAGCCACAACGTCTATATCATGGCCGACAAGCAGAAGAACGGCATCAAGGTGAACT
1861   ---------+---------+---------+---------+---------+---------+ 1920
         TGTTGTCGGTGTTGCAGATATAGTACCGGCTGTTCGTCTTCTTGCCGTAGTTCCACTTGA
             N   S   H   N   V   Y   I   M   A   D   K   Q   K   N   G   I   K   V   N   F -

TCAAGATCCGCCACAACATCGAGGACGGCAGCGTGCAGCTCGCCGACCACTACCAGCAGA
1921   ---------+---------+---------+---------+---------+---------+ 1980
         AGTTCTAGGCGGTGTTGTAGCTCCTGCCGTCGCACGTCGAGCGGCTGGTGATGGTCGTCT
             K   I   R   H   N   I   E   D   G   S   V   Q   L   A   D   H   Y   Q   Q   N -
```

Figure 4 (cont'd)

```
       ACACCCCCATCGGCGACGGCCCCGTGCTGCTGCCCGACAACCACTACCTGAGCACCCAGT
  1981 ---------+---------+---------+---------+---------+---------+ 2040
       TGTGGGGGTAGCCGCTGCCGGGGCACGACGACGGGCTGTTGGTGATGGACTCGTGGGTCA
c        T  P  I  G  D  G  P  V  L  L  P  D  N  H  Y  L  S  T  Q  S  -

CCGCCCTGAGCAAAGACCCCAACGAGAAGCGCGATCACATGGTCCTGCTGGAGTTCGTGA
  2041 ---------+---------+---------+---------+---------+---------+ 2100
       GGCGGGACTCGTTTCTGGGGTTGCTCTTCGCGCTAGTGTACCAGGACGACCTCAAGCACT
c        A  L  S  K  D  P  N  E  K  R  D  H  M  V  L  L  E  F  V  T  -
                                              MluI
                                                |
       CCGCCGCCGGGATCACTCTCGGCATGGACGAGCTGTACAAGTAACGCGTTGACTAAGCTA
  2101 ---------+---------+---------+---------+---------+---------+ 2160
       GGCGGCGGCCCTAGTGAGAGCCGTACCTGCTCGACATGTTCATTGCGCAACTGATTCGAT
c        A  A  G  I  T  L  G  M  D  E  L  Y  K  *                  -
       BssHII
          |
       TGGCGCGCACTAGGGGCTAGAGTCGGGGCGGCCGGCCGCTTCGAGCAGACATGATAAGAT
  2161 ---------+---------+---------+---------+---------+---------+ 2220
       ACCGCGCGTGATCCCCGATCTCAGCCCCGCCGGCCGGCGAAGCTCGTCTGTACTATTCTA

ACATTGATGAGTTTGGACAAACCACAACTAGAATGCAGTGAAAAAAATGCTTTATTTGTG
  2221 ---------+---------+---------+---------+---------+---------+ 2280
       TGTAACTACTCAAACCTGTTTGGTGTTGATCTTACGTCACTTTTTTTACGAAATAAACAC

AAATTTGTGATGCTATTGCTTTATTTGTAACCATTATAAGCTGCAATAAACAAGTTAACA
  2281 ---------+---------+---------+---------+---------+---------+ 2340
       TTTAAACACTACGATAACGAAATAAACATTGGTAATATTCGACGTTATTTGTTCAATTGT

ACAACAATTGCATTCATTTTATGTTTCAGGTTCAGGGGGAGGTGTGGGAGGTTTTTTAAA
  2341 ---------+---------+---------+---------+---------+---------+ 2400
       TGTTGTTAACGTAAGTAAAATACAAAGTCCAAGTCCCCCTCCACACCCTCCAAAAAATTT

GCAAGTAAAACCTCTACAAATGTGGTAAAATCGATAAGGATCGATCCGTCGACCGATGCC
  2401 ---------+---------+---------+---------+---------+---------+ 2460
       CGTTCATTTTGGAGATGTTTACACCATTTTAGCTATTCCTAGCTAGGCAGCTGGCTACGG

CTTGAGAGCCTTCAACCCAGTCAGCTCCTTCCGGTGGGCGCGGGGCATGACTATCGTCGC
  2461 ---------+---------+---------+---------+---------+---------+ 2520
       GAACTCTCGGAAGTTGGGTCAGTCGAGGAAGGCCACCCGCGCCCCGTACTGATAGCAGCG
                                                          AfeI
                                                            |
       CGCACTTATGACTGTCTTCTTTATCATGCAACTCGTAGGACAGGTGCCGGCAGCGCTCTT
  2521 ---------+---------+---------+---------+---------+---------+ 2580
       GCGTGAATACTGACAGAAGAAATAGTACGTTGAGCATCCTGTCCACGGCCGTCGCGAGAA

CCGCTTCCTCGCTCACTGACTCGCTGCGCTCGGTCGTTCGGCTGCGGCGAGCGGTATCAG
  2581 ---------+---------+---------+---------+---------+---------+ 2640
       GGCGAAGGAGCGAGTGACTGAGCGACGCGAGCCAGCAAGCCGACGCCGCTCGCCATAGTC

CTCACTCAAAGGCGGTAATACGGTTATCCACAGAATCAGGGGATAACGCAGGAAAGAACA
  2641 ---------+---------+---------+---------+---------+---------+ 2700
       GAGTGAGTTTCCGCCATTATGCCAATAGGTGTCTTAGTCCCCTATTGCGTCCTTTCTTGT
```

Figure 4 (cont'd)

```
            TGTGAGCAAAAGGCCAGCAAAAGGCCAGGAACCGTAAAAAGGCCGCGTTGCTGGCGTTTT
    2701    ---------+---------+---------+---------+---------+---------+  2760
            ACACTCGTTTTCCGGTCGTTTTCCGGTCCTTGGCATTTTTCCGGCGCAACGACCGCAAAA

TCCATAGGCTCCGCCCCCTGACGAGCATCACAAAAATCGACGCTCAAGTCAGAGGTGGC
    2761    ---------+---------+---------+---------+---------+---------+  2820
            AGGTATCCGAGGCGGGGGGACTGCTCGTAGTGTTTTTAGCTGCGAGTTCAGTCTCCACCG

GAAACCCGACAGGACTATAAAGATACCAGGCGTTTCCCCCTGGAAGCTCCCTCGTGCGCT
    2821    ---------+---------+---------+---------+---------+---------+  2880
            CTTTGGGCTGTCCTGATATTTCTATGGTCCGCAAAGGGGGACCTTCGAGGGAGCACGCGA

CTCCTGTTCCGACCCTGCCGCTTACCGGATACCTGTCCGCCTTTCTCCCTTCGGGAAGCG
    2881    ---------+---------+---------+---------+---------+---------+  2940
            GAGGACAAGGCTGGGACGGCGAATGGCCTATGGACAGGCGGAAAGAGGGAAGCCCTTCGC

TGGCGCTTTCTCATAGCTCACGCTGTAGGTATCTCAGTTCGGTGTAGGTCGTTCGCTCCA
    2941    ---------+---------+---------+---------+---------+---------+  3000
            ACCGCGAAAGAGTATCGAGTGCGACATCCATAGAGTCAAGCCACATCCAGCAAGCGAGGT

AGCTGGGCTGTGTGCACGAACCCCCCGTTCAGCCCGACCGCTGCGCCTTATCCGGTAACT
    3001    ---------+---------+---------+---------+---------+---------+  3060
            TCGACCCGACACACGTGCTTGGGGGGCAAGTCGGGCTGGCGACGCGGAATAGGCCATTGA

ATCGTCTTGAGTCCAACCCGGTAAGACACGACTTATCGCCACTGGCAGCAGCCACTGGTA
    3061    ---------+---------+---------+---------+---------+---------+  3120
            TAGCAGAACTCAGGTTGGGCCATTCTGTGCTGAATAGCGGTGACCGTCGTCGGTGACCAT

ACAGGATTAGCAGAGCGAGGTATGTAGGCGGTGCTACAGAGTTCTTGAAGTGGTGGCCTA
    3121    ---------+---------+---------+---------+---------+---------+  3180
            TGTCCTAATCGTCTCGCTCCATACATCCGCCACGATGTCTCAAGAACTTCACCACCGGAT

ACTACGGCTACACTAGAAGAACAGTATTTGGTATCTGCGCTCTGCTGAAGCCAGTTACCT
    3181    ---------+---------+---------+---------+---------+---------+  3240
            TGATGCCGATGTGATCTTCTTGTCATAAACCATAGACGCGAGACGACTTCGGTCAATGGA

TCGGAAAAGAGTTGGTAGCTCTTGATCCGGCAAACAAACCACCGCTGGTAGCGGTGGTT
    3241    ---------+---------+---------+---------+---------+---------+  3300
            AGCCTTTTTCTCAACCATCGAGAACTAGGCCGTTTGTTTGGTGGCGACCATCGCCACCAA

TTTTTGTTTGCAAGCAGCAGATTACGCGCAGAAAAAAAGGATCTCAAGAAGATCCTTTGA
    3301    ---------+---------+---------+---------+---------+---------+  3360
            AAAAACAAACGTTCGTCGTCTAATGCGCGTCTTTTTTTCCTAGAGTTCTTCTAGGAAACT

TCTTTTCTACGGGGTCTGACGCTCAGTGGAACGAAAACTCACGTTAAGGGATTTTGGTCA
    3361    ---------+---------+---------+---------+---------+---------+  3420
            AGAAAAGATGCCCCAGACTGCGAGTCACCTTGCTTTTGAGTGCAATTCCCTAAAACCAGT

TGAGATTATCAAAAAGGATCTTCACCTAGATCCTTTTAAATTAAAAATGAAGTTTTAAAT
    3421    ---------+---------+---------+---------+---------+---------+  3480
            ACTCTAATAGTTTTTCCTAGAAGTGGATCTAGGAAAATTTAATTTTTACTTCAAAATTTA
```

Figure 4 (cont'd)

```
            CAATCTAAAGTATATATGAGTAAACTTGGTCTGACAGTTACCAATGCTTAATCAGTGAGG
    3481    ---------+---------+---------+---------+---------+---------+   3540
            GTTAGATTTCATATATACTCATTTGAACCAGACTGTCAATGGTTACGAATTAGTCACTCC
                                                *   W   H   K   I   L   S   -

CACCTATCTCAGCGATCTGTCTATTTCGTTCATCCATAGTTGCCTGACTCCCCGTCGTGT
    3541    ---------+---------+---------+---------+---------+---------+   3600
            GTGGATAGAGTCGCTAGACAGATAAAGCAAGTAGGTATCAACGGACTGAGGGGCAGCACA
            A   G   I   E   A   I   Q   R   N   R   E   D   M   T   A   Q   S   G   T   T   -

AGATAACTACGATACGGGAGGGCTTACCATCTGGCCCCAGTGCTGCAATGATACCGCGAG
    3601    ---------+---------+---------+---------+---------+---------+   3660
            TCTATTGATGCTATGCCCTCCCGAATGGTAGACCGGGGTCACGACGTTACTATGGCGCTC
            Y   I   V   V   I   R   S   P   K   G   D   P   G   L   A   A   I   I   G   R   -

ACCCACGCTCACCGGCTCCAGATTTATCAGCAATAAACCAGCCAGCCGGAAGGGCCGAGC
    3661    ---------+---------+---------+---------+---------+---------+   3720
            TGGGTGCGAGTGGCCGAGGTCTAAATAGTCGTTATTTGGTCGGTCGGCCTTCCCGGCTCG
            S   G   R   E   G   A   G   S   K   D   A   I   F   W   G   A   P   L   A   S   -

AseI
                                                        |
            GCAGAAGTGGTCCTGCAACTTTATCCGCCTCCATCCAGTCTATTAATTGTTGCCGGGAAG
    3721    ---------+---------+---------+---------+---------+---------+   3780
            CGTCTTCACCAGGACGTTGAAATAGGCGGAGGTAGGTCAGATAATTAACAACGGCCCTTC
            R   L   L   P   G   A   V   K   D   A   E   M   W   D   I   L   Q   Q   R   S   -

CTAGAGTAAGTAGTTCGCCAGTTAATAGTTTGCGCAACGTTGTTGCCATTGCTACAGGCA
    3781    ---------+---------+---------+---------+---------+---------+   3840
            GATCTCATTCATCAAGCGGTCAATTATCAAACGCGTTGCAACAACGGTAACGATGTCCGT
            A   L   T   L   L   E   G   T   L   L   K   R   L   T   T   A   M   A   V   P   -

TCGTGGTGTCACGCTCGTCGTTTGGTATGGCTTCATTCAGCTCCGGTTCCCAACGATCAA
    3841    ---------+---------+---------+---------+---------+---------+   3900
            AGCACCACAGTGCGAGCAGCAAACCATACCGAAGTAAGTCGAGGCCAAGGGTTGCTAGTT
            M   T   T   D   R   E   D   N   P   I   A   E   N   L   E   P   E   W   R   D   -

GGCGAGTTACATGATCCCCCATGTTGTGCAAAAAAGCGGTTAGCTCCTTCGGTCCTCCGA
    3901    ---------+---------+---------+---------+---------+---------+   3960
            CCGCTCAATGTACTAGGGGGTACAACACGTTTTTTCGCCAATCGAGGAAGCCAGGAGGCT
            L   R   T   V   H   D   G   M   N   H   L   F   A   T   L   E   K   P   G   G   -

TCGTTGTCAGAAGTAAGTTGGCCGCAGTGTTATCACTCATGGTTATGGCAGCACTGCATA
    3961    ---------+---------+---------+---------+---------+---------+   4020
            AGCAACAGTCTTCATTCAACCGGCGTCACAATAGTGAGTACCAATACCGTCGTGACGTAT
            I   T   T   L   L   N   A   A   T   N   D   S   M   T   I   A   A   S   C   -

ATTCTCTTACTGTCATGCCATCCGTAAGATGCTTTTCTGTGACTGGTGAGTACTCAACCA
    4021    ---------+---------+---------+---------+---------+---------+   4080
            TAAGAGAATGACAGTACGGTAGGCATTCTACGAAAAGACACTGACCACTCATGAGTTGGT
            L   E   R   V   T   M   G   D   T   L   H   K   E   T   V   P   S   Y   E   V   -

AGTCATTCTGAGAATAGTGTATGCGGCGACCGAGTTGCTCTTGCCCGGCGTCAATACGGG
    4081    ---------+---------+---------+---------+---------+---------+   4140
            TCAGTAAGACTCTTATCACATACGCCGCTGGCTCAACGAGAACGGGCCGCAGTTATGCCC
            L   D   N   Q   S   Y   H   I   R   R   G   L   Q   E   Q   G   A   D   I   R   -
```

Figure 4 (cont'd)

```
                                                              XmnI
                                                               |
         ATAATACCGCGCCACATAGCAGAACTTTAAAAGTGCTCATCATTGGAAAACGTTCTTCGG
4141     ---------+---------+---------+---------+---------+---------+ 4200
         TATTATGGCGCGGTGTATCGTCTTGAAATTTTCACGAGTAGTAACCTTTTGCAAGAAGCC
          S  L  V  A  G  C  L  L  V  K  F  T  S  M  M  P  F  R  E  E   -

GGCGAAAACTCTCAAGGATCTTACCGCTGTTGAGATCCAGTTCGATGTAACCCACTCGTG
4201     ---------+---------+---------+---------+---------+---------+ 4260
         CCGCTTTTGAGAGTTCCTAGAATGGCGACAACTCTAGGTCAAGCTACATTGGGTGAGCAC
          P  R  F  S  E  L  I  K  G  S  N  L  D  L  E  I  Y  G  V  R   -

CACCCAACTGATCTTCAGCATCTTTTACTTTCACCAGCGTTTCTGGGTGAGCAAAAACAG
4261     ---------+---------+---------+---------+---------+---------+ 4320
         GTGGGTTGACTAGAAGTCGTAGAAAATGAAAGTGGTCGCAAAGACCCACTCGTTTTTGTC
          A  G  L  Q  D  E  A  D  K  V  K  V  L  T  E  P  H  A  F  V   -

GAAGGCAAAATGCCGCAAAAAAGGGAATAAGGGCGACACGGAAATGTTGAATACTCATAC
4321     ---------+---------+---------+---------+---------+---------+ 4380
         CTTCCGTTTTACGGCGTTTTTTCCCTTATTCCCGCTGTGCCTTTACAACTTATGAGTATG
          P  L  C  F  A  A  F  F  P  I  L  A  V  R  F  H  Q  I  S  M   -

TCTTCCTTTTTCAATATTATTGAAGCATTTATCAGGGTTATTGTCTCATGAGCGGATACA
4381     ---------+---------+---------+---------+---------+---------+ 4440
         AGAAGGAAAAAGTTATAATAACTTCGTAAATAGTCCCAATAACAGAGTACTCGCCTATGT

TATTTGAATGTATTTAGAAAAATAAACAAATAGGGGTTCCGCGCACATTTCCCCGAAAAG
4441     ---------+---------+---------+---------+---------+---------+ 4500
         ATAAACTTACATAAATCTTTTTATTTGTTTATCCCCAAGGCGCGTGTAAAGGGGCTTTTC
         TGCCACCTGACGCGCCCTGTAGCGGCGCATTAAGCGCGGCGGGTGTGGTGGTTACGCGCA
4501     ---------+---------+---------+---------+---------+---------+ 4560
         ACGGTGGACTGCGCGGGACATCGCCGCGTAATTCGCGCCGCCCACACCACCAATGCGCGT

GCGTGACCGCTACACTTGCCAGCGCCCTAGCGCCCGCTCCTTTCGCTTTCTTCCCTTCCT
4561     ---------+---------+---------+---------+---------+---------+ 4620
         CGCACTGGCGATGTGAACGGTCGCGGGATCGCGGGCGAGGAAAGCGAAAGAAGGGAAGGA

TTCTCGCCACGTTCGCCGGCTTTCCCCGTCAAGCTCTAAATCGGGGGCTCCCTTTAGGGT
4621     ---------+---------+---------+---------+---------+---------+ 4680
         AAGAGCGGTGCAAGCGGCCGAAAGGGGCAGTTCGAGATTTAGCCCCCGAGGGAAATCCCA

TCCGATTTAGTGCTTTACGGCACCTCGACCCCAAAAAACTTGATTAGGGTGATGGTTCAC
4681     ---------+---------+---------+---------+---------+---------+ 4740
         AGGCTAAATCACGAAATGCCGTGGAGCTGGGGTTTTTTGAACTAATCCCACTACCAAGTG

GTAGTGGGCCATCGCCCTGATAGACGGTTTTTCGCCCTTTGACGTTGGAGTCCACGTTCT
4741     ---------+---------+---------+---------+---------+---------+ 4800
         CATCACCCGGTAGCGGGACTATCTGCCAAAAAGCGGGAAACTGCAACCTCAGGTGCAAGA

TTAATAGTGGACTCTTGTTCCAAACTGGAACAACACTCAACCCTATCTCGGTCTATTCTT
4801     ---------+---------+---------+---------+---------+---------+ 4860
         AATTATCACCTGAGAACAAGGTTTGACCTTGTTGTGAGTTGGGATAGAGCCAGATAAGAA
```

Figure 4 (cont'd)

```
        TTGATTTATAAGGGATTTTGCCGATTTCGGCCTATTGGTTAAAAAATGAGCTGATTTAAC
4861    ------------------------------------------------------------  4920
        AACTAAATATTCCCTAAAACGGCTAAAGCCGGATAACCAATTTTTTACTCGACTAAATTG

AAAAATTTAACGCGAATTTTAACAAAATATTAACGCTTACAATTTGCCATTCGCCATTCA
4921    ------------------------------------------------------------  4980
        TTTTTAAATTGCGCTTAAAATTGTTTTATAATTGCGAATGTTAAACGGTAAGCGGTAAGT

HRGB4
        GGCTGCGCAACTGTTGGGAAGGGCGATCGGTGCGGGCCTCTTCGCTATTACGCCAGCCCA
4981    ------------------------------------------------------------  5040
        CCGACGCGTTGACAACCCTTCCCGCTAGCCACGCCCGGAGAAGCGATAATGCGGTCGGGT

NotI
              HRGB3                                    |
        AGCTACCATGATAAGTAAGTAATATTAAGGTACGGGAGGTACTTGGAGCGGCCGCAATAA
5041    ------------------------------------------------------------  5100
        TCGATGGTACTATTCATTCATTATAATTCCATGCCCTCCATGAACCTCGCCGGCGTTATT

AATATCTTTATTTTCATTACATCTGTGTGTTGGTTTTTTGTGTGAATCGATAGTACTAAC
5101    ------------------------------------------------------------  5160
        TTATAGAAATAAAAGTAATGTAGACACACAACCAAAAAACACACTTAGCTATCATGATTG

HRGB2
        ATACGCTCTCCATCAAAACAAAACGAAACAAAACAAACTAGCAAAATAGGCTGTCCCCAG
5161    ------------------------------------------------------------  5220
        TATGCGAGAGGTAGTTTTGTTTTGCTTTGTTTTGTTTGATCGTTTTATCCGACAGGGGTC

HRGB1
        TGCAAGTGCAGGTGCCAGAACATTTCTCTATCGATA
5221    ------------------------------------  5256
        ACGTTCACGTCCACGGTCTTGTAAAGAGATAGCTAT
```

Figure 4 (cont'd)

Enzymes that do cut and were not excluded:

| AarI | Acc65I | AfeI | AhdI | AloI | AlwNI | AseI | BamHI |
|---|---|---|---|---|---|---|---|
| BmgBI | BsaAI | BsaHI | BsaXI | BseRI | BseYI | BssHII | BstBI |
| BstEII | DraIII | EcoRI | FalI | KpnI | MluI | NotI | PfoI |
| PstI | SacII | SapI | SmaI | XhoI | XmaI | XmnI | |

Enzymes that do not cut:

| AatII | AflII | AgeI | AlfI | ApaI | AscI | AsiSI | AvrII |
|---|---|---|---|---|---|---|---|
| BaeI | BbeI | BbvCI | BclI | BfrBI | BlpI | BmtI | BplI |
| BsiWI | BsmBI | BspEI | BstAPI | BstXI | BstZ17I | Bsu36I | CspCI |
| EcoNI | EcoO109I | EcoRV | FspAI | KasI | MscI | NarI | NdeI |
| NheI | NruI | NsiI | PacI | PasI | PflMI | PmeI | PmlI |
| PpuMI | PspOMI | PspXI | PsrI | PvuII | RsrII | SanDI | SbfI |
| SexAI | SfiI | SfoI | SgrAI | SnaBI | SpeI | SrfI | StuI |
| SwaI | Tth111I | XbaI | XcmI | ZraI | | | |

Enzymes excluded; MinCuts: 1  MaxCuts: 1

| AccI | AclI | AcuI | AflIII | AleI | AloI | ApaLI | ApoI |
|---|---|---|---|---|---|---|---|
| AvaI | BanI | BanII | BbsI | BcgI | BcgI | BciVI | BglI |
| BglII | Bme1580I | BmrI | BpmI | BpuI0I | BpuEI | BsaI | BsaBI |
| BsaWI | BsaXI | BsgI | BsiEI | BsiHKAI | BsmI | Bsp1286I | BspHI |
| BspMI | BsrBI | BsrDI | BsrFI | BsrGI | BssSI | BstYI | BtgI |
| BtgZI | BtsI | ClaI | DraI | DrdI | EaeI | EagI | EarI |
| EciI | EcoICRI | Eco57MI | FseI | FspI | HaeII | HinfI | Hin4I |
| HincII | HindIII | HpaI | MfeI | MmeI | MslI | MspA1I | NaeI |
| NcoI | NgoMIV | NspI | PciI | PpiI | PpiI | PshAI | PsiI |
| PvuI | SacI | SalI | ScaI | SfcI | SmlI | SphI | SspI |
| StyI | TaqII | TaqII | TatI | | | | |

Figure 5

SEQUENCE LISTING

```
<160> NUMBER OF SEQ ID NOS: 3

<210> SEQ ID NO 1
<211> LENGTH: 5256
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (190)..(207)
<223> OTHER INFORMATION: n is a, c, g, or t
<220> FEATURE:
<221> NAME/KEY: CDS
<222> LOCATION: (214)..(897)
<220> FEATURE:
<221> NAME/KEY: CDS
<222> LOCATION: (1425)..(2141)

<400> SEQUENCE: 1
ggtaccgagc tcaagcttcg gagtactgtc ctccgagcgg agtactgtcc tccgagcgga      60
gtactgtcct ccgagcggag tactgtcctc cgttcgaaag cggaccctg gcaggaggaa     120 ggtcagcaga gctgctgata agagccgtat aaagagggtt ccgctcgcaa agatctatgg    180
catgaattcn nnnnnnnnn nnnnnnngga tcc atg gtg aag ctg tct tct atc      234
                                    Met Val Lys Leu Ser Ser Ile
                                    1               5 gaa caa gca tgc gat att tgc cga ctt aaa aag ctc aag tgc tcc aaa      282
Glu Gln Ala Cys Asp Ile Cys Arg Leu Lys Lys Leu Lys Cys Ser Lys
        10              15                  20 gaa aaa ccg aag tgc gcc aag tgt ctg aag aac aac tgg gag tgt cgc      330
Glu Lys Pro Lys Cys Ala Lys Cys Leu Lys Asn Asn Trp Glu Cys Arg
    25              30                  35 tac tct ccc aaa acc aaa agg tct ccg ctg act agg gca cat ctg aca      378
Tyr Ser Pro Lys Thr Lys Arg Ser Pro Leu Thr Arg Ala His Leu Thr
40              45                  50                  55 gaa gtg gaa tca agg cta gaa aga ctg gaa cag cta ttt cta ctg att      426
Glu Val Glu Ser Arg Leu Glu Arg Leu Glu Gln Leu Phe Leu Leu Ile
                60                  65                  70 ttt cct cga gaa gac ctt gac atg att ttg aaa atg gat tct tta cag      474
Phe Pro Arg Glu Asp Leu Asp Met Ile Leu Lys Met Asp Ser Leu Gln
            75                  80                  85 gat ata aaa gca ttg tta aca gga tta ttt gta caa gat aat gtg aat      522
Asp Ile Lys Ala Leu Leu Thr Gly Leu Phe Val Gln Asp Asn Val Asn
        90                  95                  100 aaa gat gcc gtc aca gat aga ttg gct tca gtg gag act gat atg cct      570
Lys Asp Ala Val Thr Asp Arg Leu Ala Ser Val Glu Thr Asp Met Pro
    105                 110                 115 cta aca ttg aga cag cat aga ata agt gcg aca tca tca tcg gaa gag      618
Leu Thr Leu Arg Gln His Arg Ile Ser Ala Thr Ser Ser Ser Glu Glu
120                 125                 130                 135 agt agt aac aaa ggt caa aga cag ttg act gta tcg att aaa gtc gcc      666
Ser Ser Asn Lys Gly Gln Arg Gln Leu Thr Val Ser Ile Lys Val Ala
                140                 145                 150 ccc ccg acc gat gtc agc ctg ggg gac gag ctc cac tta gac ggc gag      714
Pro Pro Thr Asp Val Ser Leu Gly Asp Glu Leu His Leu Asp Gly Glu
            155                 160                 165 gac gtg gcg atg gcg cat gcc gac gcg cta gac gat ttc gat ctg gac      762
```

```
                Asp Val Ala Met Ala His Ala Asp Ala Leu Asp Asp Phe Asp Leu Asp
                        170                 175                 180 atg ttg ggg gac ggg gat tcc ccg ggg ccg gga ttt acc ccc cac gac        810
Met Leu Gly Asp Gly Asp Ser Pro Gly Pro Gly Phe Thr Pro His Asp
        185                 190                 195 tcc gcc ccc tac ggc gct ctg gat atg gcc gac ttc gag ttt gag cag        858
Ser Ala Pro Tyr Gly Ala Leu Asp Met Ala Asp Phe Glu Phe Glu Gln
200                 205                 210                 215 atg ttt acc gat gcc ctt gga att gac gag tac ggt ggg taaccgcggg         907
Met Phe Thr Asp Ala Leu Gly Ile Asp Glu Tyr Gly Gly
                220                 225 ctagagtcgg ggcggccggc cgcttcgagc agacatgata agatacattg atgagtttgg      967
acaaaccaca actagaatgc agtgaaaaaa atgctttatt tgtgaaattt gtgatgctat     1027
tgctttattt gtaaccatta taagctgcaa taaacaagtt aacaacaaca attgcattca     1087
ttttatgttt caggttcagg gggaggtgtg ggaggttttt taaagcaagt aaaacctcta     1147
caaatgtggt aaaatcgata aggatcgatc cgtcgagatc tgcgatctaa gtaagcttgg     1207
ctgcaggtcg acggatcgga gtactgtcct ccgagcggag tactgtcctc cgagcggagt     1267
actgtcctcc gagcggagta ctgtcctccg agcggacccc tggcaggagg aaggtcagca     1327
gagctgctga taagagccgt ataaagaggg ttccgctcat ggcaagggc agtggtctcg      1387 ggatctgagc ttggcattcc ggtactgttg gtaaaccc atg gtg agc aag ggc gag    1442
                                              Met Val Ser Lys Gly Glu
                                                              230 gag ctg ttc acc ggg gtg gtg ccc atc ctg gtc gag ctg gac ggc gac       1490
Glu Leu Phe Thr Gly Val Val Pro Ile Leu Val Glu Leu Asp Gly Asp
235                 240                 245                 250 gta aac ggc cac aag ttc agc gtg tcc ggc gag ggc gag ggc gat gcc       1538
Val Asn Gly His Lys Phe Ser Val Ser Gly Glu Gly Glu Gly Asp Ala
                255                 260                 265 acc tac ggc aag ctg acc ctg aag ttc atc tgc acc acc ggc aag ctg       1586
Thr Tyr Gly Lys Leu Thr Leu Lys Phe Ile Cys Thr Thr Gly Lys Leu
                270                 275                 280 ccc gtg ccc tgg ccc acc ctc gtg acc acc ctg acc tac ggc gtg cag       1634
Pro Val Pro Trp Pro Thr Leu Val Thr Thr Leu Thr Tyr Gly Val Gln
            285                 290                 295 tgc ttc agc cgc tac ccc gac cac atg aag cag cac gac ttc ttc aag       1682
Cys Phe Ser Arg Tyr Pro Asp His Met Lys Gln His Asp Phe Phe Lys
300                 305                 310 tcc gcc atg ccc gaa ggc tac gtc cag gag cgc acc atc ttc ttc aag       1730
Ser Ala Met Pro Glu Gly Tyr Val Gln Glu Arg Thr Ile Phe Phe Lys
315                 320                 325                 330 gac gac ggc aac tac aag acc cgc gcc gag gtg aag ttc gag ggc gac       1778
Asp Asp Gly Asn Tyr Lys Thr Arg Ala Glu Val Lys Phe Glu Gly Asp
                335                 340                 345 acc ctg gtg aac cgc atc gag ctg aag ggc atc gac ttc aag gag gac       1826
Thr Leu Val Asn Arg Ile Glu Leu Lys Gly Ile Asp Phe Lys Glu Asp
                350                 355                 360 ggc aac atc ctg ggg cac aag ctg gag tac aac tac aac agc cac aac       1874
Gly Asn Ile Leu Gly His Lys Leu Glu Tyr Asn Tyr Asn Ser His Asn
                365                 370                 375 gtc tat atc atg gcc gac aag cag aag aac ggc atc aag gtg aac ttc       1922
Val Tyr Ile Met Ala Asp Lys Gln Lys Asn Gly Ile Lys Val Asn Phe
            380                 385                 390 aag atc cgc cac aac atc gag gac ggc agc gtg cag ctc gcc gac cac       1970
Lys Ile Arg His Asn Ile Glu Asp Gly Ser Val Gln Leu Ala Asp His
395                 400                 405                 410
```

-continued

| | | |
|---|---|---|
| tac cag cag aac acc ccc atc ggc gac ggc ccc gtg ctg ctg ccc gac<br>Tyr Gln Gln Asn Thr Pro Ile Gly Asp Gly Pro Val Leu Leu Pro Asp<br>415 420 425 | 2018 | |
| aac cac tac ctg agc acc cag tcc gcc ctg agc aaa gac ccc aac gag<br>Asn His Tyr Leu Ser Thr Gln Ser Ala Leu Ser Lys Asp Pro Asn Glu<br>430 435 440 | 2066 | |
| aag cgc gat cac atg gtc ctg ctg gag ttc gtg acc gcc gcc ggg atc<br>Lys Arg Asp His Met Val Leu Leu Glu Phe Val Thr Ala Ala Gly Ile<br>445 450 455 | 2114 | |
| act ctc ggc atg gac gag ctg tac aag taacgcgttg actaagctat<br>Thr Leu Gly Met Asp Glu Leu Tyr Lys<br>460 465 | 2161 | | ggcgcgcact aggggctaga gtcggggcgg ccggccgctt cgagcagaca tgataagata 2221 cattgatgag tttggacaaa ccacaactag aatgcagtga aaaaaatgct ttatttgtga 2281 aatttgtgat gctattgctt tatttgtaac cattataagc tgcaataaac aagttaacaa 2341 caacaattgc attcatttta tgtttcaggt tcaggggag gtgtgggagg ttttttaaag 2401 caagtaaaac ctctacaaat gtggtaaaat cgataaggat cgatccgtcg accgatgccc 2461 ttgagagcct tcaacccagt cagctccttc cggtgggcgc ggggcatgac tatcgtcgcc 2521 gcacttatga ctgtcttctt tatcatgcaa ctcgtaggac aggtgccggc agcgctcttc 2581 cgcttcctcg ctcactgact cgctgcgctc ggtcgttcgg ctgcggcgag cggtatcagc 2641 tcactcaaag gcggtaatac ggttatccac agaatcaggg gataacgcag gaaagaacat 2701 gtgagcaaaa ggccagcaaa aggccaggaa ccgtaaaaag gccgcgttgc tggcgttttt 2761 ccataggctc cgcccccctg acgagcatca caaaaatcga cgctcaagtc agaggtggcg 2821 aaacccgaca ggactataaa gataccaggc gtttccccct ggaagctccc tcgtgcgctc 2881 tcctgttccg accctgccgc ttaccggata cctgtccgcc tttctccctt cgggaagcgt 2941 ggcgctttct catagctcac gctgtaggta tctcagttcg gtgtaggtcg ttcgctccaa 3001 gctgggctgt gtgcacgaac cccccgttca gcccgaccgc tgcgccttat ccggtaacta 3061 tcgtcttgag tccaacccgg taagacacga cttatcgcca ctggcagcag ccactggtaa 3121 caggattagc agagcgaggt atgtaggcgg tgctacagag ttcttgaagt ggtggcctaa 3181 ctacggctac actagaagaa cagtatttgg tatctgcgct ctgctgaagc cagttacctt 3241 cggaaaaaga gttggtagct cttgatccgg caaacaaacc accgctggta gcggtggttt 3301 ttttgtttgc aagcagcaga ttacgcgcag aaaaaaagga tctcaagaag atcctttgat 3361 cttttctacg gggtctgacg ctcagtggaa cgaaaactca cgttaaggga ttttggtcat 3421 gagattatca aaaaggatct tcacctagat ccttttaaat taaaaatgaa gttttaaatc 3481 aatctaaagt atatatgagt aaacttggtc tgacagttac caatgcttaa tcagtgaggc 3541 acctatctca gcgatctgtc tatttcgttc atccatagtt gcctgactcc ccgtcgtgta 3601 gataactacg atacgggagg gcttaccatc tggccccagt gctgcaatga taccgcgaga 3661 cccacgctca ccggctccag atttatcagc aataaaccag ccagccggaa gggccgagcg 3721 cagaagtggt cctgcaactt tatccgcctc catccagtct attaattgtt gccgggaagc 3781 tagagtaagt agttcgccag ttaatagttt gcgcaacgtt gttgccattg ctacaggcat 3841 cgtggtgtca cgctcgtcgt ttggtatggc ttcattcagc tccggttccc aacgatcaag 3901 gcgagttaca tgatccccca tgttgtgcaa aaaagcggtt agctccttcg gtcctccgat 3961 cgttgtcaga agtaagttgg ccgcagtgtt atcactcatg gttatggcag cactgcataa 4021 ttctcttact gtcatgccat ccgtaagatg cttttctgtg actggtgagt actcaaccaa 4081

```
gtcattctga gaatagtgta tgcggcgacc gagttgctct tgcccggcgt caatacggga    4141
taataccgcg ccacatagca gaactttaaa agtgctcatc attggaaaac gttcttcggg    4201
gcgaaaactc tcaaggatct taccgctgtt gagatccagt tcgatgtaac ccactcgtgc    4261
acccaactga tcttcagcat cttttacttt caccagcgtt tctgggtgag caaaaacagg    4321
aaggcaaaat gccgcaaaaa agggaataag ggcgacacgg aaatgttgaa tactcatact    4381
cttccttttt caatattatt gaagcattta tcagggttat tgtctcatga gcggatacat    4441
atttgaatgt atttagaaaa ataaacaaat aggggttccg cgcacatttc cccgaaaagt    4501
gccacctgac gcgccctgta gcggcgcatt aagcgcggcg ggtgtggtgg ttacgcgcag    4561
cgtgaccgct acacttgcca gcgccctagc gcccgctcct ttcgctttct tcccttcctt    4621
tctcgccacg ttcgccggct ttccccgtca gctctaaat cggggggctcc ctttagggtt    4681 ccgatttagt gctttacggc acctcgaccc caaaaaactt gattagggtg atggttcacg    4741
tagtgggcca tcgccctgat agacggtttt tcgccctttg acgttggagt ccacgttctt    4801
taatagtgga ctcttgttcc aaactggaac aacactcaac cctatctcgg tctattcttt    4861
tgatttataa gggattttgc cgatttcggc ctattggtta aaaaatgagc tgatttaaca    4921
aaaatttaac gcgaatttta acaaaatatt aacgcttaca atttgccatt cgccattcag    4981
gctgcgcaac tgttgggaag ggcgatcggt gcgggcctct tcgctattac gccagcccaa    5041
gctaccatga taagtaagta atattaaggt acggaggta cttggagcgg ccgcaataaa    5101
atatctttat tttcattaca tctgtgtgtt ggttttttgt gtgaatcgat agtactaaca    5161
tacgctctcc atcaaaacaa aacgaaacaa aacaaactag caaaataggc tgtccccagt    5221
gcaagtgcag gtgccagaac atttctctat cgata                              5256
```

<210> SEQ ID NO 2
<211> LENGTH: 467
<212> TYPE: PRT
<213> ORGANISM: Artificial sequence
<220> FEATURE:
<223> OTHER INFORMATION: Synthetic Construct

<400> SEQUENCE: 2

```
Met Val Lys Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Ile Lys Val Ala Pro Pro Thr Asp Val Ser Leu Gly Asp
```

```
            145                 150                 155                 160
        Glu Leu His Leu Asp Gly Glu Asp Val Ala Met Ala His Ala Asp Ala
                        165                 170                 175
        Leu Asp Asp Phe Asp Leu Asp Met Leu Gly Asp Gly Asp Ser Pro Gly
                        180                 185                 190
        Pro Gly Phe Thr Pro His Asp Ser Ala Pro Tyr Gly Ala Leu Asp Met
                        195                 200                 205
        Ala Asp Phe Glu Phe Glu Gln Met Phe Thr Asp Ala Leu Gly Ile Asp
                        210                 215                 220
        Glu Tyr Gly Gly Met Val Ser Lys Gly Glu Leu Phe Thr Gly Val
        225                 230                 235                 240
        Val Pro Ile Leu Val Glu Leu Asp Gly Asp Val Asn Gly His Lys Phe
                        245                 250                 255
        Ser Val Ser Gly Glu Gly Glu Gly Asp Ala Thr Tyr Gly Lys Leu Thr
                        260                 265                 270
        Leu Lys Phe Ile Cys Thr Thr Gly Lys Leu Pro Val Pro Trp Pro Thr
                        275                 280                 285
        Leu Val Thr Thr Leu Thr Tyr Gly Val Gln Cys Phe Ser Arg Tyr Pro
                        290                 295                 300
        Asp His Met Lys Gln His Asp Phe Phe Lys Ser Ala Met Pro Glu Gly
        305                 310                 315                 320
        Tyr Val Gln Glu Arg Thr Ile Phe Phe Lys Asp Asp Gly Asn Tyr Lys
                        325                 330                 335
        Thr Arg Ala Glu Val Lys Phe Glu Gly Asp Thr Leu Val Asn Arg Ile
                        340                 345                 350
        Glu Leu Lys Gly Ile Asp Phe Lys Glu Asp Gly Asn Ile Leu Gly His
                        355                 360                 365
        Lys Leu Glu Tyr Asn Tyr Asn Ser His Asn Val Tyr Ile Met Ala Asp
                        370                 375                 380
        Lys Gln Lys Asn Gly Ile Lys Val Asn Phe Lys Ile Arg His Asn Ile
        385                 390                 395                 400
        Glu Asp Gly Ser Val Gln Leu Ala Asp His Tyr Gln Gln Asn Thr Pro
                        405                 410                 415
        Ile Gly Asp Gly Pro Val Leu Leu Pro Asp Asn His Tyr Leu Ser Thr
                        420                 425                 430
        Gln Ser Ala Leu Ser Lys Asp Pro Asn Glu Lys Arg Asp His Met Val
                        435                 440                 445
        Leu Leu Glu Phe Val Thr Ala Ala Gly Ile Thr Leu Gly Met Asp Glu
                        450                 455                 460
        Leu Tyr Lys
        465

<210> SEQ ID NO 3
<211> LENGTH: 286
<212> TYPE: PRT
<213> ORGANISM: Artificial sequence
<220> FEATURE:
<223> OTHER INFORMATION: Synthetic construct

<400> SEQUENCE: 3

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
                20                  25                  30

Asp Ala Glu Asp Gln Leu Gly Ala Arg Val Gly Tyr Ile Glu Leu Asp
```

```
            35                  40                  45
Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285
```

TRANSLATION ENHANCER-ELEMENT DEPENDENT VECTOR SYSTEMS

CROSS REFERENCE TO RELATED APPLICATION(S)

This application is a continuation application of U.S. application Ser. No. 11/509,293 filed Aug. 23, 2006, now pending; which claims the benefit of priority under 35 U.S.C. §119(e) of U.S. Ser. No. 60/711,149, filed Aug. 24, 2005, the entire content of which is incorporated herein by reference.

GRANT INFORMATION

This invention was made with support from NIH Grant No. GM 61725. The government has certain rights in this invention.

INCORPORATION BY REFERENCE OF SEQUENCE LISTING

The contents of the text file named "PROO-007/C01US_Sequence Listing_ST25.txt," which was created on May 13, 2015 and is 20 KB in size, are hereby incorporated by reference in their entirety.

FIELD OF INVENTION

The present invention relates generally to vector constructs, and more specifically to positive feedback vector constructs bearing translational enhancer elements (TEEs) in combination with transcriptional elements and genes encoding transcription factors, where such constructs may be used to identify other TEEs and to modulate levels of protein expression.

BACKGROUND OF THE INVENTION

Eukaryotic mRNAs can initiate translation by either cap-dependent or cap-independent mechanisms. Presently, the relative contributions of these mechanisms to the proteome are unknown; however, some studies suggest that cap-independent mechanisms may account for the translation of many mRNAs. For some mRNAs, cap-independent translation is facilitated by sequence elements termed internal ribosome entry sites (IRESes). IRESes were first discovered in uncapped picornavirus RNAs and were subsequently identified in other viral and cellular mRNAs from mammals, insects, and yeast. For some mRNAs, IRESes facilitate translation when cap-dependent initiation is less efficient or blocked. Internal initiation also facilitates the translation of particular mRNAs with 5' leaders that are encumbered by numerous upstream AUGs or RNA secondary structures.

A variety of evidence suggests that different IRESes vary in length, sequence composition, and in their requirements for initiation factors or other trans-acting factors, suggesting that internal initiation of translation occurs by a number of different mechanisms. Some IRESes are modular in composition. For example, an IRES module from the 5' leader of the Gtx homeodomain mRNA showed that maximal activity was obtained with sequences of 7 nucleotides. Various lines of evidence suggested that the mechanism underlying the activity of this sequence element involves base pairing to a complementary sequence of 18S rRNA. In another study, a 22-nt IRES was identified in the 5' leader of the Rbm3 mRNA.

In addition, it has been reported that the 5' leader of the thymidine kinase mRNA contains an IRES-element and that the 5' leader of the c-myc mRNA contains two short IRES elements.

The short size of some IRES/TEE modules suggests that they may be prevalent within mRNA populations.

Some IRES elements can also function as translation enhancer elements (TEEs), i.e., they can enhance translation in the context of a monocistronic mRNA. However, not all TEEs are IRESes and not all IRESes are TEEs.

SUMMARY OF THE INVENTION

The present invention describes a series of vectors designed to select for translational enhancer elements and overexpression of proteins of interest, and includes methods for the use of such vectors.

In one embodiment, a nucleic acid vector including a first construct that includes two or more first transcriptional elements, a first cistron encoding a transcription factor, and one or more first translational enhancer elements (TEEs), where the transcription factor amplifies the transcription of at least one cistron of the first construct is envisaged.

In a related aspect, the vector may include, but is not limited to, at least one cistron on one or more second constructs including at least one transcriptional unit. In a further related aspect, the first construct and the at least one transcriptional unit of one or more second constructs include transcriptional elements that are targets for the transcription factor encoded by the first cistron.

In a related aspect, such vectors may encode a gene product that is a reporter protein, a therapeutic protein, an enzyme, an antigen, a structural protein, or an antibody.

In another aspect, at least one gene product blocks host protein synthesis. In a related aspect, the gene product may include, but is not limited to, NSP3, L-proteinase, or proteinase 2A.

In one aspect, the vector includes at least one TEE that is resistant to the activity of the product which blocks host protein synthesis, where the vector may contain transcriptional elements including, but not limited to, minimal promoters, regulatable promoters, upstream activating sequences, and bacteriophage RNA polymerase specific promoters.

In another embodiment, a nucleic acid vector including a first construct which includes a first transcriptional element, a first cistron encoding a first gene product, and a first translational enhancer element (TEE), wherein the TEE is resistant to an activity of a second gene product which blocks host protein synthesis is envisaged.

In a related aspect, TEEs include, HCV-IRES, IRESes, and IRES-elements, including, but not limited to, Gtx sequences (e.g., Gtx9-nt, Gtx8-nt, Gtx7-nt). In another related aspect, TEEs may include N-18 random nucleotides which when operably linked to a cistron, increase the amount of protein induced per unit mRNA.

In one embodiment, a method of identifying a translational enhancer element (TEE) is envisaged including inserting nucleotides from a library of nucleotides into a vector including a first construct which includes two or more first transcriptional elements, and a first cistron encoding a transcription factor, transfecting a cell with the vector, and determining the level of gene product translation from one or more second constructs in the transfected cell, where determining an enhanced level of translation of the gene product in the presence of the inserted nucleotides is indicative of the presence of at least one TEE.

In a related aspect, the method may further include co-transfecting the cell with one or more second vectors, wherein the second vectors include the one or more second constructs.

In another embodiment, a method of overexpressing a gene is envisaged including, transfecting a cell with a vector including a first construct including two or more first transcriptional elements, a first cistron encoding a transcription factor, and one or more first translation enhancer elements (TEEs), and expressing a gene product from one or more second constructs including a second TEE, where the resulting level of gene product expressed from the second construct is enhanced in the presence of the first and second TEEs.

In a related aspect, the method may further include co-transfecting the cell with one or more second vectors including the one or more second constructs. In a further related aspect, the method may further include expressing a gene from a third construct including a third TEE, where the gene from the third construct encodes one or more gene products which block host protein synthesis. In a related aspect, the method may further include co-transfecting the cell with a third vector including the third construct.

In one embodiment, a method of overexpressing a gene is envisaged including transfecting a cell with a vector including a first construct including at least one first transcriptional element, a first cistron encoding a first gene product, and at least one translation enhancer element (TEE) and expressing a gene from one or more second constructs encoding a protein which blocks host protein synthesis, where the resulting level of gene product expressed from the first construct is enhanced in the presence of the blocking protein.

Exemplary methods and compositions according to this invention, are described in greater detail below.

BRIEF DESCRIPTION OF THE DRAWINGS

FIG. 1 illustrates a translation enhancer-driven positive feedback vector. A schematic representation of the positive feedback vector is shown along with the various promoter (P1) and transcriptional enhancer (P2) sequences, transcription factor (TF) genes, and a protein of interest. The transcription factor gene and the gene of interest may be on the same plasmid or on different plasmids. For the selection application, a random nucleotide sequence (N), n nucleotides in length is present in the 5' leader of the transcription factor mRNA. A sequence that functions as a translational enhancer element (TEE) will facilitate the translation of this mRNA. The encoded transcription factor will then bind to sites in the promoters of the two genes and increase their transcription.

As shown in FIG. 2, each gene contains a TEE in its 5' leader. In this scenario, the TEE is resistant to the activity of the other encoded protein (e.g., NSP3). The two genes may be on one or two different plasmids.

FIG. 4 shows a restriction map for a positive feedback reporting vector (SEQ ID NO: 1). Sequences in bold represent: 1) promoter sequences, including TATA boxes and upstream activating sequences (UAS); 2) GAL4R1-GAL4R4, primer sequences for PCR amplification; 3) ATG and TAA, start and stop translation sequences, respectively; and 4) HRGB1-HRGB4, primer sequences for PCR amplification.

FIG. 5 shows one-cut enzymes for pUAS-GV16-UAS-EGFP (SEQ ID NO: 1).

DETAILED DESCRIPTION OF THE INVENTION

Figure 2:
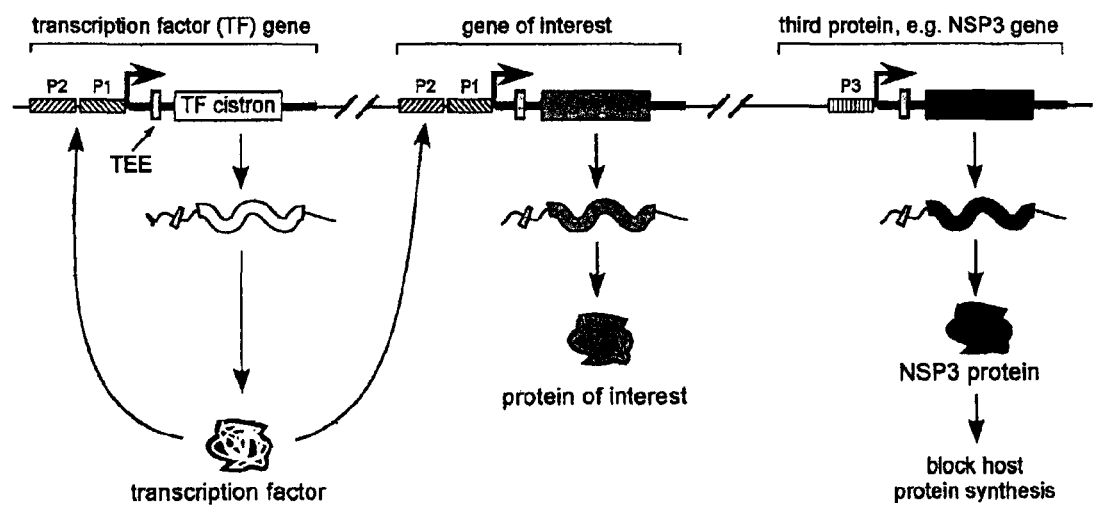
FIG. 2 illustrates a translation enhancer-driven positive feedback vector with a third protein to block host protein synthesis. The first two genes (transcription factor gene and gene of interest) are the same as in FIG. 1 except that all three mRNAs contain a TEE in their 5' leader. The third protein (e.g., the Rotavirus NSP3 protein) will increase the translation of the first two encoded mRNAs by blocking the translation of host mRNAs and reducing the competition from them. The third gene is under the transcriptional control of promoter P3, which is either a constitutive promoter or an inducible promoter. P3 may also include promoter elements P1 and P2. For the selection application, the mRNAs for the gene of interest and third protein will contain a known TEE, while the transcription factor gene will contain a random nucleotide sequence. In this scenario, the TEE is resistant to the activity of the third protein. For a protein production application, all three genes may contain a known TEE that is resistant to the activity of the third protein. The three genes may be on one, two, or three different plasmids.

Before the present compositions and methods are described, it is understood that this invention is not limited to the particular methodology, protocols, and reagents described as these may vary. It is also to be understood that the terminology used herein is for the purpose of describing particular embodiments only, and is not intended to limit the scope of the present invention which will be described by the appended claims.

It must be noted that as used herein and in the appended claims, the singular forms "a", "an", and "the" include plural reference unless the context clearly dictates otherwise. Thus, for example, reference to "a cell" includes a plurality of such cells, reference to "a protein" includes one or more proteins and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the methods, devices, and materials are now described. All publications mentioned herein are incorporated herein by reference for the purpose of describing and disclosing the proteins, nucleic acids, and methodologies which are reported in the publications which might be used in connection with the invention. Nothing herein is to be construed as an admission that the invention is not entitled to antedate such disclosure by virtue of prior invention.

As used herein, "translational enhancer element (TEE)," including grammatical variations thereof, means cis-acting sequences that increase the amount of protein induced per unit mRNA. In a related aspect, TEEs include, HCV-IRES, IRESes, and IRES-elements, including, but not limited to, Gtx sequences (e.g., Gtx9-nt, Gtx8-nt, Gtx7-nt). In another related aspect, TEEs may include N-18 random nucleotides which when operably linked to a cistron, increase the amount of protein induced per unit mRNA.

In a further related aspect, sequences for such elements include, but are not limited to, GenBank accession numbers AX205123 and AX205116 (Gtx IRES element), D17763 (HCV-IRES, 5'-untranslated region).

As used herein, "cistron" including grammatical variations thereof, means a unit of DNA that codes for a single polypeptide or protein.

As used herein, "transcriptional unit," including grammatical variations thereof, means the segment of DNA within which the synthesis of RNA occurs.

As used herein, "nucleotide sequence," "nucleic acid sequence," "nucleic acid," or "polynucleotide," refers to a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides. Nucleic acid sequences can be, e.g., prokaryotic sequences, eukaryotic mRNA sequences, cDNA sequences from eukaryotic mRNA, genomic DNA sequences from eukaryotic DNA (e.g., mammalian DNA), and synthetic DNA or RNA sequences, but are not limited thereto.

In a related aspect, synthetic methods for preparing a nucleotide sequence include, for example, the phosphotriester and phosphodiester methods (see Narang et al., Meth. Enzymol. 68:90, (1979); U.S. Pat. No. 4,356,270, U.S. Pat. No. 4,458,066, U.S. Pat. No. 4,416,988, U.S. Pat. No. 4,293, 652; and Brown et al., Meth Enzymol 68:109, (1979), each of which is incorporated herein by reference).

As used herein, "promoter" including grammatical variations thereof, means a nucleic acid sequence capable of directing transcription. A variety of promoter sequences are known in the art. For example, such elements can include, but are not limited to, TATA-boxes, CCAAT-boxes, bacteriophage RNA polymerase specific promoters (T7: TAATACGACTCACTATAGG (SEQ ID NO:4); SP6: ATTTAGGTGACACTATAGA(SEQ ID NO: 5); and T3: AATTAACCCTCACTAAAGG(SEQ ID NO:6)), an SP1 site (GGGCGG), and a cyclic AMP response element (TGACGTCA).

As used herein, "transcriptional element," including grammatical variations thereof, means a cis-acting site on DNA that allows for initiation or stimulation of initiation of transcription, usually through recognition by a transcription factor. For example, such elements exist in motifs including, but not limited to, CACGTG (c-Myc), TGAc/gTc/aA (c-Fos), and t/aGATA (GATA). In a related aspect, the vector may contain one or more transcriptional elements comprising one or more upstream activating sequences (UAS), including but not limited to, the consensus GAGTACTGTCCTCCGAGCG (SEQ ID NO: 7).

As used herein, "transcription factor," including grammatical variations thereof, means any protein required to initiate or regulate transcription. For example, such factors include, but are not limited to, c-Myc, c-Fos, c-Jun, CREB, cEts, GATA, GAL4, GAL4Np16, c-Myb, MyoD, NF-κB, bacteriophage-specific RNA polymerases, Hif-1, and TRE.

In a further related aspect, sequences for such factors include, but are not limited to, GenBank accession numbers K02276 (c-Myc), K00650 (c-fos), BC002981 (c-jun), M27691 (CREB), X14798 (cEts), M77810 (GATA), K01486 (GAL4), AY136632 (GAL4/Vp16), M95584 (c-Myb), M84918 (MyoD), 2006293A (NF-κB), NP 853568 (SP6 RNA polymerase), AAB28111 (T7 RNA polymerase), NP 523301 (T3 RNA polymerase), AF364604 (HIF-1), and X63547 (TRE).

As used herein, "transcriptional activator regions," including grammatical variations thereof, means protein sequences that, when tethered to DNA near a promoter, activate transcription by contacting targets in the transcriptional machinery (see, e.g., Xiangyang et al., Proc Natl Acad Sci USA (2000) 97:1988-1992). Activator regions, characterized by having an excess of acidic amino acid residues, are found in a wide array of eukaryotic activators, including the yeast activators Ga14, GCN4, and the herpesvirus activator VP16.

As used herein, "construct," including grammatical variations thereof, means nucleic acid sequence elements arranged in a definite pattern of organization such that the expression of genes/gene products that are operably linked to these elements can be predictably controlled. In a related aspect, a wide variety of heterologous sequences may be included in the construct, including, but not limited to, for example, sequences which encode growth factors, cytokines, chemokines, lymphokines, toxins, prodrugs, antibodies, antigens, ribozymes, as well as antisense sequences. In another related aspect, such heterologous sequences encode proteins which can serve as therapeutic modalities.

As used herein, "vector," including grammatical variations thereof, means the DNA of any transmissible agent (e.g., plasmid or virus) into which a segment of foreign DNA can be spliced in order to introduce the foreign DNA into host cells to promote its replication and/or transcription.

As disclosed herein, a vector comprising a construct is useful for identifying translational enhancer elements. In one embodiment, the construct is contained in a vector, which generally is an expression vector that contains certain components, but otherwise can vary widely in sequence and in functional element content. The vector also can contain sequences that facilitate recombinant DNA manipulations, including, for example, elements that allow propagation of the vector in a particular host cell (e.g., a bacterial cell, insect cell, yeast cell, or mammalian cell), selection of cells containing the vector (e.g., antibiotic resistance genes for selection in bacterial or mammalian cells), and cloning sites for introduction of reporter genes or the elements to be examined (e.g., restriction endonuclease sites or recombinase recognition sites).

Preferably, constructs as envisaged provide the advantage that the activity of an oligonucleotide can be examined in the context or milieu of the whole eukaryotic chromosome. A chromosome offers unique and complex regulatory features with respect to the control of gene expression, including translation. As such, it is advantageous to have a system and method for obtaining regulatory oligonucleotides that function in the context of a chromosome. Thus, a method of the invention can be practiced such that integration of the expression vector into the eukaryotic host cell chromosome occurs, forming a stable construct prior to selection for an expressed reporter molecule.

A vector comprising a construct as envisaged can be integrated into a chromosome by a variety of methods and under a variety of conditions. Thus, the present invention should not be construed as limited to the exemplified methods. Shotgun transfection, for example, can result in stable integration if selection pressure is maintained upon the transfected cell through several generations of cell division, during which time the transfected nucleic acid construct becomes stably integrated into the cell genome. Directional vectors, which can integrate into a host cell chromosome and form a stable integrant, also can be used. These vectors can be based on targeted homologous recombination, which restricts the site of integration to regions of the chromosome having the homology, and can be based on viral vectors, which can randomly associate with the chromosome and form a stable integrant, or can utilize site specific recombination methods and reagents such as a lox-Cre system and the like.

Shotgun transfections can be accomplished by a variety of well known methods, including, for example, electroporation, calcium phosphate mediated transfection, DEAE dextran mediated transfection, a biolistic method, a lipofectin method, and the like. For random shotgun transfections, the culture conditions are maintained for several generations of cell division to ensure that a stable integration has resulted and, generally, a selective pressure also is applied. A viral vector based integration method also can be used and provides the advantage that the method is more rapid and establishes a stable integration by the first generation of cell division. A viral vector based integration also provides the advantage that the transfection (infection) can be performed at a low vector:cell ratio, which increases the probability of single copy transfection of the cell. A single copy expression vector in the cell during selection increases the reliability that an observed regulatory activity is due to a particular oligonucleotide, and facilitates isolation of such an oligonucleotides.

Reference is made herein to techniques commonly known in the art. Guidance in the application of such techniques can be found, e.g., in Ausubel et al. eds., 1995, Current Protocols In Molecular Biology, and in Sambrook et al., 1989, Molecular Cloning: A Laboratory Manual, Cold Spring Harbor Laboratory Press, NY, the contents of which are incorporated herein by reference.

Previous studies have generated synthetic IRESes containing multiple individual IRES elements and showed that this multimerization led to higher, and in some cases exponential, increases in IRES activity. To facilitate the discovery process, a number of methods to screen for IRES elements in mammalian cells and in yeast have been developed. In all of these methods, dicistronic mRNAs containing a library of random nucleotide sequences in the intercistronic sequences (ICS) were expressed in cells, and those cells containing IRES elements were identified on the basis of the expression of the second cistron. The mammalian methods used a fluorescent reporter protein as the second cistron, and positive cells were identified with FACS. However, a limitation of these methods was that the activities of individual IRES elements were relatively low, leading to a large number of false positive cells.

To circumvent this signal-to-noise problem, the present invention describes a positive feedback based system where one cistron encoding a TEE containing transcription factor triggers a positive feedback loop in which the transcription factor binds to a select sequence in the upstream promoter of the cistron encoding the factor and one or more cistrons encoding an mRNA of interest, thereby increasing the transcription of both mRNAs. More mRNA results in more transcription factor, leading to ever-increasing amounts of both the transcription factor and protein of interest mRNA and the encoded proteins.

In one embodiment, the vector system is a translation enhancer-driven positive feedback vector (e.g., see FIG. 1). In one aspect, a construct expresses two mRNAs: one encoding a protein of interest which may be a reporter protein and the other encoding a transcription factor. The transcription of both mRNAs is driven by minimal promoters but can be enhanced by the expression of the transcription factor via binding sites for the transcription factor that are located in the promoters of both genes. A small amount of transcription factor mRNA is expressed from the minimal promoter but the translation of this mRNA is blocked by an obstacle in the 5' leader of the mRNA encoding the transcription factor. This obstacle may be a stable stem-loop structure and/or upstream AUG initiation codons. The synthesis of this transcription factor is dependent on the presence of a translation enhancer in the mRNA encoding this factor.

The translational enhancer can be located in the 5' leader of the mRNA, downstream of the inhibitory elements but upstream of the initiation codon, or it may be located in the 3' untranslated region (UTR). In one aspect, the TEE is situated in the 5' leader sequence which is contained within a cistron.

Utilization of this vector system may require that the encoded transcription factor not be expressed in the cells of interest. For example, a transcription factor (e.g., Ga14Np16), that contains the DNA binding domain of the yeast GAL4 transcription factor is suitable for use in mammalian cells because mammalian genes do not appear to be targets of this transcription factor. Other suitable transcription factors include, but are not limited to, those that are expressed endogenously at very low levels, or are absent in the cells of interest. For example, bacteriophage specific-RNA polymerases (e.g., T7, T3, and SP6 RNA polymerases) are suitable for use in both mammalian cells and yeast. The genes as envisaged can be encoded by one or more vectors.

In one embodiment, the vector system can be used to identify a TEE. An oligonucleotide to be examined for translational activity can be operatively linked to an expressible polynucleotide, which, for example, can encode a reporter molecule. As used herein, the term "operatively linked" means that a regulatory element, which can be a synthetic regulatory oligonucleotide or an oligonucleotide to be examined for such activity, is positioned with respect to a translatable nucleotide sequence such that the regulatory element can affect its regulatory activity. An oligonucleotide having translational enhancer activity generally is positioned within about 1 to 500 nucleotides, particularly within about 1 to 100 nucleotides of a translation start site.

A library of randomized oligonucleotides to be examined for translational regulatory activity can be provided, and one or more individual members of the library can be cloned into multiple copies of the construct of the vector. The oligonucleotide to be examined for translational regulatory activity is introduced such that it is operatively linked to the minimal promoter element in the construct and, therefore, has the potential to function as a TEE. In this way, a library of different constructs, which can be contained in a vector, is formed, each construct differing in the introduced potential regulatory oligonucleotide sequence.

Oligonucleotides to be examined for translational regulatory activity can be, for example, cDNA sequences encoding 5' UTRs of cellular mRNAs, including a library of such cDNA molecules. Furthermore, as disclosed herein, TEEs identified according to a method of the invention, including synthetic TEE elements, have been found to be complementary to oligonucleotide sequences of ribosomal RNA, particularly to un-base paired oligonucleotide sequences of rRNA, which are interspersed among double stranded regions that form due to hybridization of self complementary sequences within rRNA. Accordingly, oligonucleotides to be examined for translational regulatory activity, can be designed based on their being complementary to an oligonucleotide sequence of rRNA, particularly to an un-base paired oligonucleotide sequence of rRNA such as a yeast, mouse or human rRNA (e.g., see GenBank Accession Nos. V01335, X00686, X03205, each of which is incorporated herein by reference). In addition, oligonucleotides to be examined for translational regulatory activity can be a library of variegated oligonucleotide sequences (see, for example, U.S. Pat. No. 5,837,500, incorporated herein by reference), which can be based, for example, on a translational enhancer element as disclosed herein or identified using a method of the invention, or on an oligonucleotide sequence complementary to an un-base paired region of a rRNA.

The oligonucleotides identified herein as having translational regulatory activity provide modules that can be used alone or combined with each other to produce desired activities. For example, concatemers of an identified TEE can vastly increase polypeptide expression from an associated cistron, including concatemers of 2, 5, 10, 20, 35, 50 or 75 copies of a TEE, which independently can be multiple copies of the same or different TEEs, and which can be operatively linked adjacent to each other or separated by spacer nucleotide sequences that can vary from 1 to about 100 nucleotides in length.

A synthetic translational regulatory element can be identified by screening, for example, a library of oligonucleotides containing a large number of different nucleotide sequences. The oligonucleotides can be variegated oligonucleotide sequences, which are based on but different from a known translational regulatory element, for example, an oligonucleotide complementary to an un-base paired sequence of a rRNA, or can be a random oligonucleotide library. The use of randomized oligonucleotides (e.g., N18) provides the advantage that no prior knowledge is required of the nucleotide sequence, and provides the additional advantage that completely new regulatory elements can be identified. Methods for making a combinatorial library of nucleotide sequences or a variegated population of nucleotide sequences are well known in the art (see, for example, U.S. Pat. No. 5,837,500; U.S. Pat. No. 5,622,699; U.S. Pat. No. 5,206,347; Scott and Smith, Science 249:386-390, 1992; Markland et al., Gene 109:13 19, 1991; O'Connell et al., Proc Natl Acad Sci, USA 93:5883-5887, 1996; Tuerk and Gold, Science 249:505-510, 1990; Gold et al., Ann Rev Biochem 64:763-797, 1995; each of which is incorporated herein by reference).

A synthetic TEE oligonucleotide, which can be obtained using a method of the invention, can increase or decrease the level of translation of an mRNA containing the oligonucleotide. In particular, a TEE oligonucleotide can selectively regulate translation in a context specific manner, depending, for example, on the cell type for expression, the nature of the TEE sequence, or the presence of other effector sequences in the construct.

A regulatory element can be of various lengths from a few nucleotides to several hundred nucleotides. Thus, the length of an oligonucleotide in a library of oligonucleotides to be screened can be any length, including oligonucleotides as short as about 6 nucleotides or as long as about 100 nucleotides or more. Generally, the oligonucleotides to be examined are about 6, 12, 18, 30 nucleotides or the like in length. The complexity of the library, i.e., the number of unique members, also can vary, although preferably the library has a high complexity so as to increase the likelihood that regulatory sequences are present. Libraries can be made using any method known in the art, including, for example, using an oligonucleotide synthesizer and standard oligonucleotide synthetic chemistry. Where the oligonucleotides are to be incorporated into a vector, the library complexity depends in part on the size of the expression vector population being used to clone the random library and transfect cells. Thus, a theoretical limitation for the complexity of the library also relates to utilization of the library content by the recipient expression vector and by the transfected cells, as well as by the complexity that can be obtained using a particular method of oligonucleotide synthesis.

To identify TEEs, libraries of constructs that contain either random nucleotide sequences or cDNA segments of 5' leaders of mRNAs are introduced into cells. Cells containing a construct with a TEE upstream of the transcription factor will trigger the positive feedback mechanism and produce large amounts of both proteins. If one of the proteins is a reporter protein, its activity can be readily assayed. For example, if the reporter is enhanced green fluorescent protein (EGFP), fluorescence activated cell sorting (FACS) can be used to identify cells expressing the fluorescent protein. In a preferred embodiment of the present invention, the means of detecting the presence of GFP in transfected cells is by fluorescence microscopy and by FACS. However, it will be readily understood by those of skill in the art that other means for detecting the presence of GFP may also be used in the practice of the present invention. The means of detecting GFP or of tracking or monitoring cells which have been transfected with a construct of the present invention may be any means whereby the presence GFP protein is detectable. For example, optical imaging, infrared imaging of gene expression, and flow cytometry may also be used.

In a related aspect, other reporter proteins can include, but are not limited to, enhanced yellow fluorescent protein (EYFP), enhanced cyan fluorescent protein (ECFP), luciferase, β-galactosidase, β-glucuronidase, alkaline phosphatase, and chloramphenicol acetyltransferase.

In a related aspect, such a vector can be used to identify sequences that enhance translation by various mechanisms, including but not limited to, cap-independent and cap-dependent mechanisms.

In one aspect, the vector system as envisaged can be used to overexpress another protein of interest. In a related aspect, the mRNA encoding the transcription factor will contain a known TEE. Such a system may be suitable for the batch production of proteins, where the transcription factor is under the control of a regulatable promoter, so that cells can be grown to a large volume before the positive feed back mechanisms and large scale protein production are induced by, for example, an inducing agent.

The term "inducing agent" is used to refer to a chemical, biological or physical agent that effects translation from an inducible translational regulatory element. In response to exposure to an inducing agent, translation from the element generally is initiated de novo or is increased above a basal or constitutive level of expression. Such induction can be identified using the methods disclosed herein, including detecting an increased level of a reporter polypeptide encoded by the expressible polynucleotide that is operatively linked to the TEE. An inducing agent can be, for example, a stress condition to which a cell is exposed, for example, a heat or cold shock, a toxic agent such as a heavy metal ion, or a lack of a nutrient, hormone, growth factor, or the like; or can be exposure to a molecule that affects the growth or differentiation state of a cell such as a hormone or a growth factor. As disclosed herein, the translational regulatory activity of an oligonucleotide can be examined in cells that are exposed to particular conditions or agents, or in cells of a particular cell type, and oligonucleotides that have translational regulatory activity in response to and only under the specified conditions or in a specific cell type can be identified.

In another embodiment, a vector system is envisaged which expresses a third mRNA that encodes a protein that can increase the translation of the other two encoded mRNAs by decreasing the translation of cellular mRNAs (FIG. 2). In one aspect, the expression of the third protein decreases competition from the cellular mRNAs and leads to an increased signal-to-noise ratio in the selection application.

In a related aspect, the third protein may be a viral protein that blocks translation of host mRNAs and thereby decreases the competition arising from these mRNAs. Viral proteins include, but are not limited to, NSP3, L-proteinase, or proteinase 2A. For example, without being bound to theory, the NSP3 protein blocks cap-dependent translation by binding to the eukaryotic initiation factor 4G (eIF4G) with high affinity, displacing the poly(A) binding protein, disrupting mRNA circulation, and dramatically decreasing efficiency. In this scenario, the three vector encoded mRNAs contain features that prevent their translation from being blocked. For example, where a TEE does not require eIF4G for activity, such an element would be resistant to NSP3 (e.g., Gtx IRES elements and the Cricket paralysis virus IRES). In a related aspect, the third protein can be under the control of the encoded transcription factor or under the control of an inducible promoter.

Figure 3:
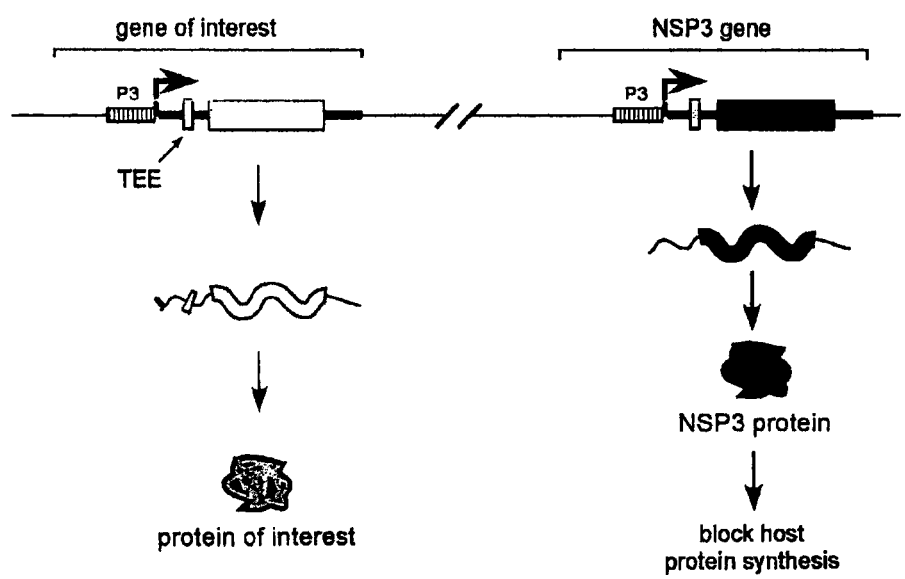
FIG. 3 illustrates a protein overexpression vector. The first gene encodes the gene of interest.

In one embodiment, the vector system expresses a gene product or protein of interest and a third protein, where the third protein blocks host protein synthesis (FIG. 3). In a related aspect, the gene product or protein of interest will contain features that prevent their translation from being blocked. In another related aspect, the genes are transcribed by either a constitutive promoter or an inducible promoter.

A kit of the invention is also envisaged. Such a kit can contain a packaging material, for example, a container having a TEE containing oligonucleotide according to the invention and a label that indicates uses of the oligonucleotide for regulating translation of a polynucleotide in an expression vector or other expression construct. In one embodiment, the system, preferably in kit form, provides an integrating expression vector for use in selecting a TEE oligonucleotide using a method as disclosed herein. Such a kit can contain a packaging material, which comprises a container having an integrating expression vector and a label that indicates uses of the vector for selecting oligonucleotide sequences capable of regulatory function.

Instructions for use of the packaged components also can be included in a kit of the invention. Such instructions for use generally include a tangible expression describing the components, for example, a TEE containing oligonucleotide, including its concentration and sequence characteristics, and can include a method parameter such as the manner by which the reagent can by utilized for its intended purpose. The reagents, including the oligonucleotide, which can be contained in a vector or operably linked to an expressible polynucleotide, can be provided in solution, as a liquid dispersion, or as a substantially dry powder, for example, in a lyophilized form. The packaging materials can be any materials customarily utilized in kits or systems, for example, materials that facilitate manipulation of the regulatory oligonucleotides and, if present, of the vector, which can be an expression vector. The package can be any type of package, including a solid matrix or material such as glass, plastic (e.g., polyethylene, polypropylene, and polycarbonate), paper, foil, or the like, which can hold within fixed limits a reagent such as a TEE containing oligonucleotide or vector. Thus, for example, a package can be a bottle, vial, plastic and plastic-foil laminated envelope, or the like container used to contain a contemplated reagent. The package also can comprise one or more containers for holding different components of the kit.

The following examples are intended to illustrate but not limit the invention.

EXAMPLES

Example 1

Experimental Procedures/Materials

Construction of Vectors

The constructs used in the present invention express one or more cistronic mRNAs that encode a transcription factor, protein of interest and/or a protein blocking host protein synthesis. Promoters used to drive transcription of the cistronic mRNAs consist of a minimal promoter (TATA box) or regulatable promoter, alone or in combination with one or more other transcriptional elements, including upstream activating sequences (UAS) and bacteriophage specific promoters. For feedback vectors, a first cistron would comprise a gene encoding a transcription factor, which is inserted downstream from a known or unknown TEE. One such construct, containing a known TEE, would comprise a TATA box promoter element, one or more UAS sequences, and one or more Gtx modules upstream from a cistron encoding Gal4/Vp16.

Example 2

Positive Feedback Reporter Vector for Identifying TEE elements

Construction

As shown in FIG. 4, the promoters used to drive transcription in this example comprise a minimal promoter (TATA box) in combination with four copies of the GAL4 upstream activating sequence (UAS). The first transcription unit encodes the GAL4/VP16 fusion protein and the second transcription unit encodes EGFP. The TEE insertion site (denoted by "N" in FIG. 4) contains nucleotides from a library of 18 random nucleotides. The vector backbone is based on plasmid pHRG-B (Promega, Madison, Wis.). The original BamHI site in pHRG-B was mutated so that both EcoRI and BamHI sites in the TEE insertion site were unique. The random $N_{18}$ fragments are cloned into this reporter vector by using the EcoRI and BamHI restriction sites.

Cell Culture and Transfection Analysis

Reporter constructs are transfected into Chinese hamster ovary cells (CHO) ($2 \times 10^4$) by using FuGENE 6™ (Roche, Alameda, Calif.). Transfection efficiencies are normalized by co-transfection with a LacZ reporter gene construct (pC-MVβ, Clontech, Mountainview, Calif.). Cells are harvested 3 days after transfection and sorted by FACS on a FACSVantage SE™ (Becton Dickinson, Franklin Lakes, N.J.) (Also, see Owens et al., Proc Natl Acad Sci USA (2004) 101:9590-9594). β-galactosidase assays may be performed by methods known in the art. For example, see Chappell et al., Proc Natl Acad Sci USA (2000) 97:1536-1541.

Double-stranded oligonucleotides containing N18 sequences are cloned into the TEE assay site of the positive feedback vector by using EcoRI and BamHI restriction sites. Overnight ligations are performed using T4 DNA ligase at 16° C. The resulting ligation mix is transfected into CHO cells, and FACS analysis is performed as above. For each FACS analysis, the first 100,000 cells are analyzed and a sorting window is drawn to select the cells with the highest EGFP expression. DNA is extracted from cells recovered by FACS and PCR reactions are carried-out by using primers to sequences that flank the EcoRI and BamHI restriction sites. After digestion with both EcoRI and BamHI restriction enzymes, the resulting fragments are re-cloned into the same amplification vector and retested.

For determining the number of plasmids per transfected cell, equal amounts of two plasmids are mixed, CMV-EGFP and CMV-enhanced cyan fluorescent protein (CMV-ECFP; Clontech, Mountainview, Calif.). The cloning vector pBluescript-KS II™ (Stratagene, La Jolla, Calif.) is used as filler for co-transfection. CHO cells are transfected with the different mixtures and FACS analysis is performed 2 days later to assess the expression of both EGFP and ECFP.

All of the compositions and methods disclosed and claimed herein can be made and executed without undue experimentation in light of the present disclosure. While the compositions and methods of this invention have been described in terms of illustrative embodiments, it will be apparent to those of skill in the art that variations may be applied to the composition, methods and in the steps or in the sequence of steps of the methods described herein without departing from the concept, spirit, and scope of the invention. More specifically, it will be apparent that certain agents which are both chemically and physiologically related may be substituted for the agents described herein while the same or similar results would be achieved. Although the invention has been described with reference to the above examples, it will be understood that modifications and variations are encompassed within the spirit and scope of the invention.

What is claimed is:

1. A polycistronic vector suitable for use in a mammalian host cell comprising:
   a) an isolated first polynucleotide construct comprising in an operable manner in a 5' to 3' direction: (i) two or more first transcriptional elements comprising a TATA box promoter element comprising nucleotides 148-153 of SEQ ID NO:1 in combination with four copies of the GAL4 upstream activating sequence (UAS) comprising nucleotides 19-35, 38-54, 57-73, and 76-92 of SEQ ID NO:1, (ii) at least one first translational enhancer elements (TEEs) comprising one N18 random oligonucleotide sequence comprising nucleotides 190-207 of SEQ ID NO:1, and (iii) a first cistron comprising nucleotides 214-897 of SEQ ID NO:1 and encoding a first gene product, wherein the first gene product is a yeast regulatory protein GAL4/viral fusion protein 16 (GAL4/VP16), and wherein said N18 is operably linked to the first cistron and increases the amount of GAL4/viral protein induced per unit mRNA as related to the absence of said N18 random oligonucleotide sequence;
   b) an isolated second polynucleotide construct comprising in an operable manner in a 5' to 3' direction: (i) at least one second transcriptional element comprising a TATA box promoter element comprising nucleotides 1347-1352 of SEQ ID NO:1 in combination with four copies of the GAL4/UAS comprising nucleotides 1224-1240, 1243-1259, 1262-1278, and 1281-1297 of SEQ ID NO:1, (ii) at least a second TEEs comprising internal ribosome entry sites (IRES) elements having translational regulatory activity, and (iii) a second cistron encoding a second gene product, wherein the second TEEs is operably linked to the second cistron; and
   c) an isolated third polynucleotide construct comprising in an operable manner in a 5' to 3' direction: (i) at least one third transcriptional element, (ii) at least a third TEEs comprising internal ribosome entry sites (IRES) elements having translational regulatory activity, and (iii) a third cistron encoding a third gene product, wherein said third TEEs is operable linked to the third cistron, wherein said third gene product is selected from the group consisting of a Rotavirus NSP3 protein, L-proteinase, and proteinase 2A,
   wherein the first, second, and third constructs are functionally linked, wherein the expression of the GAL4/VP16 results in binding to GAL4 upstream activating sequence (UAS) sites in the transcriptional element promoters of the first and second polynucleotide sequences and increases their transcription, wherein the resulting level of gene product expressed from the second polynucleotide construct is enhanced in the presence of the first and second TEEs, and wherein expression of the third gene product increases the translation of the first and second cistron by decreasing the competition arising from cellular mRNAs in a mammalian host cell.

2. The vector of claim 1, wherein the IRES element in the second or third TEEs is a Gtx sequence.

3. The vector of claim 1, wherein the second cistron encodes a reporter protein, therapeutic protein, an enzyme, an antigen, an antibody, or a structural protein.

4. The vector of claim 3, wherein the reporter protein is GFP, luciferase, b-galactosidase, b-glucuronidase, alkaline phosphatase, chloramphenicol acetyltransferase, ECFP, EGFP, or EYFP.

* * * * *